United States Patent
Vijayachandran et al.

(10) Patent No.: US 11,980,392 B2
(45) Date of Patent: May 14, 2024

(54) PINCH-TO-CLAMP CANNULA DEPTH LIMITER

(71) Applicant: Cilag GmbH International, Zug (CH)

(72) Inventors: Sajayesh Vijayachandran, Kannur (IN); Arunachalam Muthuchidambaram, Madurai (IN)

(73) Assignee: Cilag GmbH International, Zug (CH)

( * ) Notice: Subject to any disclaimer, the term of this patent is extended or adjusted under 35 U.S.C. 154(b) by 66 days.

(21) Appl. No.: 17/213,401

(22) Filed: Mar. 26, 2021

(65) Prior Publication Data

US 2021/0338273 A1    Nov. 4, 2021

(30) Foreign Application Priority Data

May 1, 2020    (IN) ............................. 202011018669

(51) Int. Cl.
*A61B 17/34*    (2006.01)
*A61B 17/00*    (2006.01)

(52) U.S. Cl.
CPC ....... *A61B 17/3423* (2013.01); *A61B 2017/00367* (2013.01); *A61B 2017/3429* (2013.01); *A61B 2017/347* (2013.01)

(58) Field of Classification Search
CPC ............ A61B 17/3421; A61B 17/3423; A61B 17/0218
See application file for complete search history.

(56) References Cited

U.S. PATENT DOCUMENTS

| | | | |
|---|---|---|---|
| 3,817,251 | A | 6/1974 | Hasson |
| 4,699,616 | A | 10/1987 | Nowak et al. |
| 5,002,557 | A | 3/1991 | Hasson |

(Continued)

FOREIGN PATENT DOCUMENTS

| | | |
|---|---|---|
| AU | 702882 B2 | 3/1993 |
| CN | 106344126 B | 2/2019 |

(Continued)

OTHER PUBLICATIONS

International Search Report and Written Opinion dated Jul. 22, 2021, for International Application No. PCT/EP2021/061421, 15 pages.

(Continued)

*Primary Examiner* — Si Ming Ku
(74) *Attorney, Agent, or Firm* — Frost Brown Todd LLP

(57) ABSTRACT

A depth limiter that is configured to couple with a cannula tube of a trocar. The depth limiter includes a body having first and second body portions coupled together and pivotable between open and clamped configurations. The body includes first and second inner surfaces presented by the first and second body portions. In the clamped configuration the first and second inner surfaces form a first cross dimension sized to restrict axial movement of the depth limiter relative to the cannula tube. In the open configuration the first and second inner surfaces form a second cross dimension sized to permit axial movement of the depth limiter relative to the cannula tube. The depth limiter includes first and second locking members, one of which is resiliently biased to engage the other. The locking members are configured to engage each other to lock the body portions in the clamped configuration.

20 Claims, 19 Drawing Sheets

(56) References Cited

U.S. PATENT DOCUMENTS

| | | |
|---|---|---|
| 5,147,316 A | 9/1992 | Castillenti |
| 5,215,531 A | 6/1993 | Maxson et al. |
| D338,270 S | 8/1993 | Stephens et al. |
| 5,256,147 A | 10/1993 | Vidal et al. |
| 5,257,975 A | 11/1993 | Foshee |
| 5,263,939 A | 11/1993 | Wortrich |
| 5,267,970 A | 12/1993 | Chin et al. |
| 5,290,249 A | 3/1994 | Foster et al. |
| 5,364,372 A | 11/1994 | Danks et al. |
| D354,562 S | 1/1995 | Medema |
| 5,540,675 A | 7/1996 | Hasson |
| 5,697,913 A | 12/1997 | Sierocuk et al. |
| 5,792,135 A | 8/1998 | Madhani et al. |
| 5,800,451 A | 9/1998 | Buess et al. |
| 5,817,061 A | 10/1998 | Goodwin et al. |
| 5,833,666 A | 11/1998 | Davis et al. |
| 5,836,913 A | 11/1998 | Orth et al. |
| 5,855,566 A | 1/1999 | Dunlap et al. |
| 5,951,588 A | 9/1999 | Moenning |
| 5,957,888 A | 9/1999 | Hinchcliffe |
| 6,432,085 B1 | 8/2002 | Stellon et al. |
| 6,451,041 B1 | 9/2002 | Moenning et al. |
| 6,632,197 B2 | 10/2003 | Lyon |
| 6,638,265 B1 | 10/2003 | Ternamian |
| 6,808,492 B2 | 10/2004 | Snyder |
| 7,235,064 B2 | 6/2007 | Hopper et al. |
| 7,981,092 B2 | 7/2011 | Duke |
| 8,147,453 B2 | 4/2012 | Albrecht et al. |
| 8,226,553 B2 | 7/2012 | Shelton, IV et al. |
| 8,251,900 B2 | 8/2012 | Ortiz et al. |
| 8,287,503 B2 | 10/2012 | Albrecht et al. |
| 8,479,969 B2 | 7/2013 | Shelton, IV |
| 8,568,362 B2 | 10/2013 | Moreno, Jr. et al. |
| 8,573,465 B2 | 11/2013 | Shelton, IV |
| 8,579,807 B2 | 11/2013 | Moreno, Jr. et al. |
| 8,636,686 B2 | 1/2014 | Minnelli et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 8,939,946 B2 | 1/2015 | Albrecht et al. |
| 9,259,238 B2 | 2/2016 | Albrecht et al. |
| 9,522,265 B2 | 12/2016 | Pravong et al. |
| 10,327,805 B2 | 6/2019 | Hibner et al. |
| 10,327,809 B2 | 6/2019 | Buyda et al. |
| 10,792,069 B2 | 10/2020 | Hall et al. |
| 10,820,924 B2 | 11/2020 | Hall et al. |
| 2005/0113856 A1 | 5/2005 | Epstein et al. |
| 2005/0165432 A1 | 7/2005 | Heinrich |
| 2007/0225643 A1 | 9/2007 | Hopper et al. |
| 2009/0182282 A1 | 7/2009 | Okihisa et al. |
| 2010/0010449 A1 | 1/2010 | Leibowitz et al. |
| 2010/0057010 A1 | 3/2010 | Göransson |
| 2012/0227221 A1* | 9/2012 | Whitaker ........... A61M 39/1011 29/525.08 |
| 2013/0060084 A1 | 3/2013 | Fouts et al. |
| 2014/0066953 A1 | 3/2014 | Keating et al. |
| 2016/0015423 A1 | 1/2016 | Ravikumar et al. |
| 2017/0311932 A1 | 11/2017 | Rebellino |
| 2018/0199959 A1 | 7/2018 | Lee |
| 2018/0206883 A1 | 7/2018 | McIntyre et al. |
| 2018/0214140 A1 | 8/2018 | Nock et al. |
| 2019/0000496 A1 | 1/2019 | Shelton, IV et al. |
| 2019/0083071 A1 | 3/2019 | Rebellino et al. |
| 2019/0150900 A1 | 5/2019 | Choung et al. |
| 2019/0254703 A1 | 8/2019 | Ciampini et al. |
| 2019/0254704 A1 | 8/2019 | Buyda et al. |
| 2019/0282793 A1* | 9/2019 | Stafford ............... A61M 39/08 |
| 2019/0380742 A1 | 12/2019 | Hall et al. |
| 2020/0080675 A1* | 3/2020 | White ..................... F16L 35/00 |
| 2020/0205855 A1* | 7/2020 | Aravalli ............ A61B 17/3496 |
| 2021/0338269 A1 | 11/2021 | Scott et al. |
| 2021/0338272 A1 | 11/2021 | Muthuchidambaram et al. |
| 2021/0338274 A1 | 11/2021 | Scott et al. |
| 2021/0338275 A1 | 11/2021 | Vijayachandran |
| 2021/0338276 A1 | 11/2021 | Scott |
| 2021/0338278 A1 | 11/2021 | Scott et al. |
| 2021/0338281 A1 | 11/2021 | Mozloom, Jr. et al. |
| 2021/0338282 A1 | 11/2021 | Vijayachandran |
| 2021/0338283 A1 | 11/2021 | McLain |
| 2021/0338371 A1 | 11/2021 | Harris et al. |

FOREIGN PATENT DOCUMENTS

| | | |
|---|---|---|
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

* cited by examiner

PINCH-TO-CLAMP CANNULA DEPTH LIMITER

PRIORITY

This application claims priority to Indian Provisional Patent App. No. 202011018669, entitled "Pinch-To-Clamp Cannula Depth Limiter," filed May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
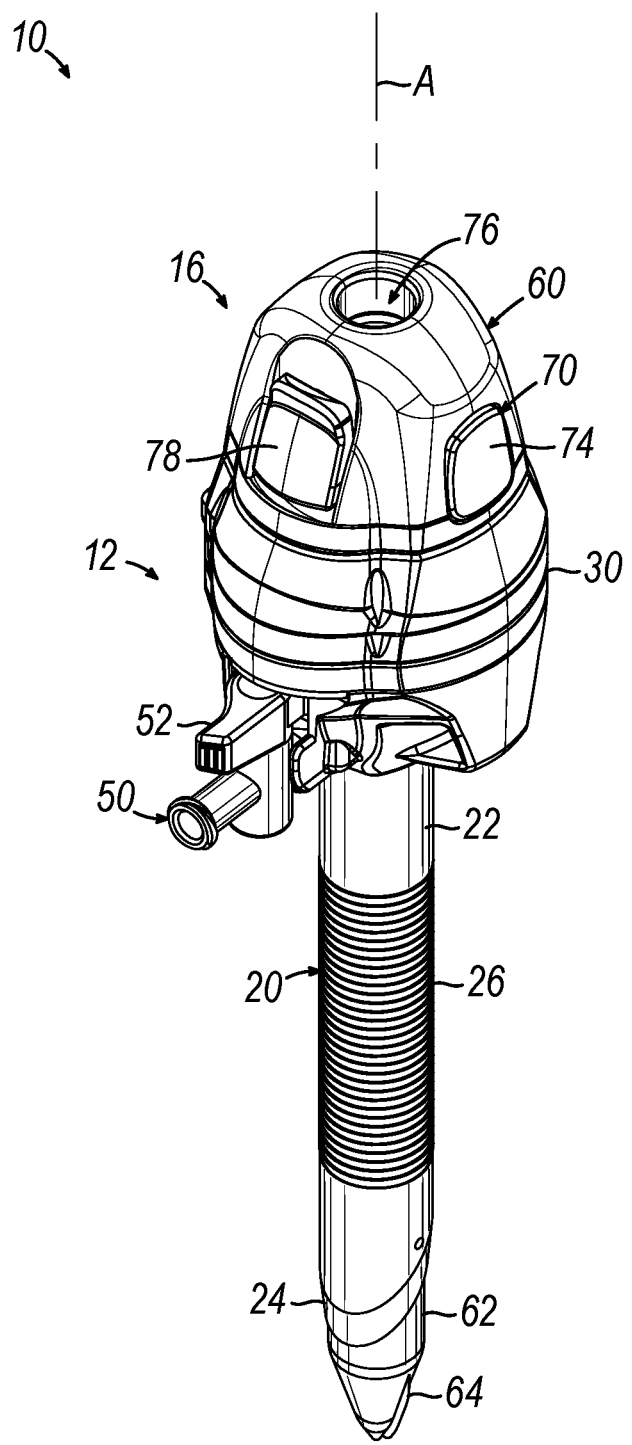
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
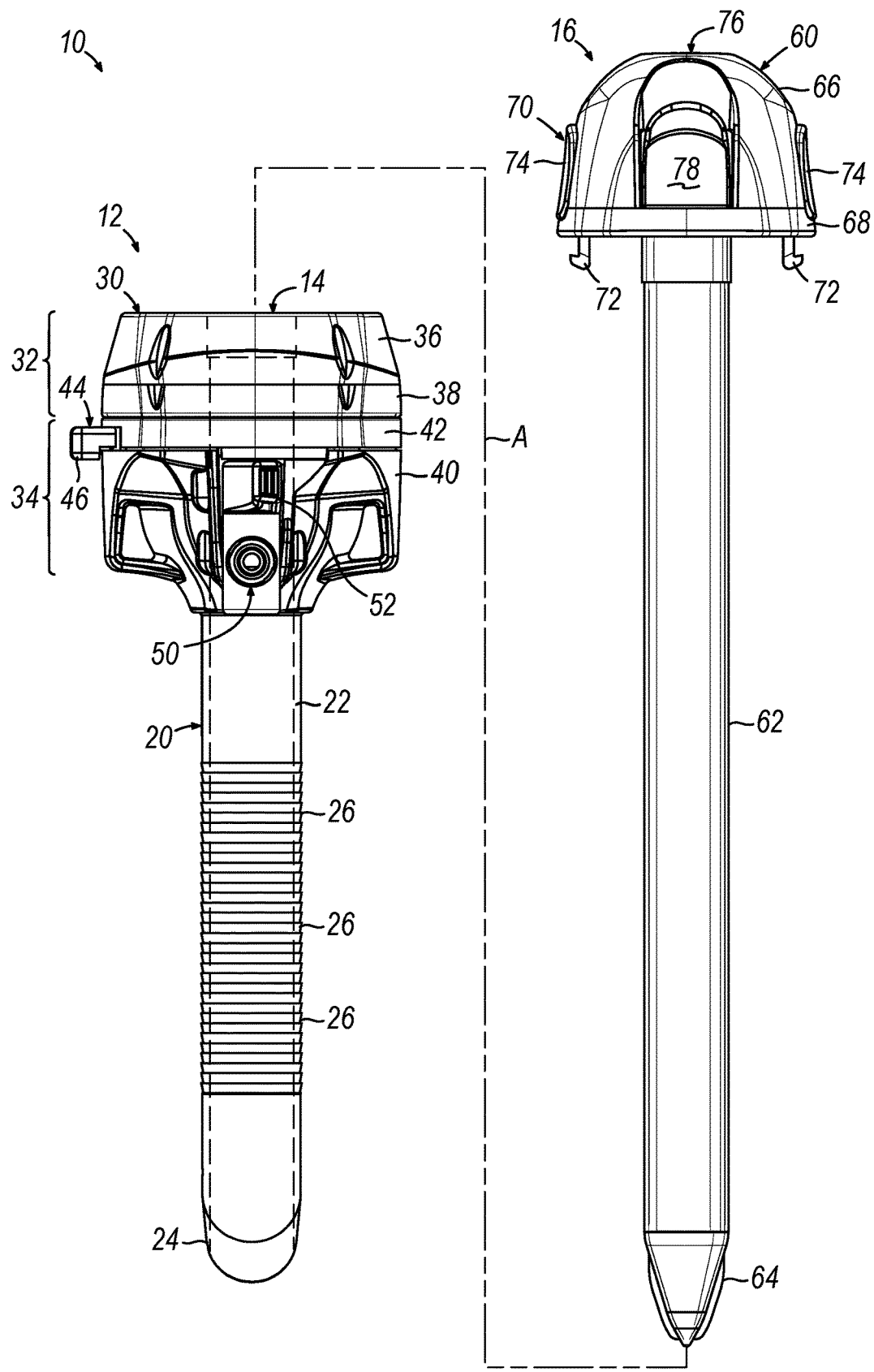
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
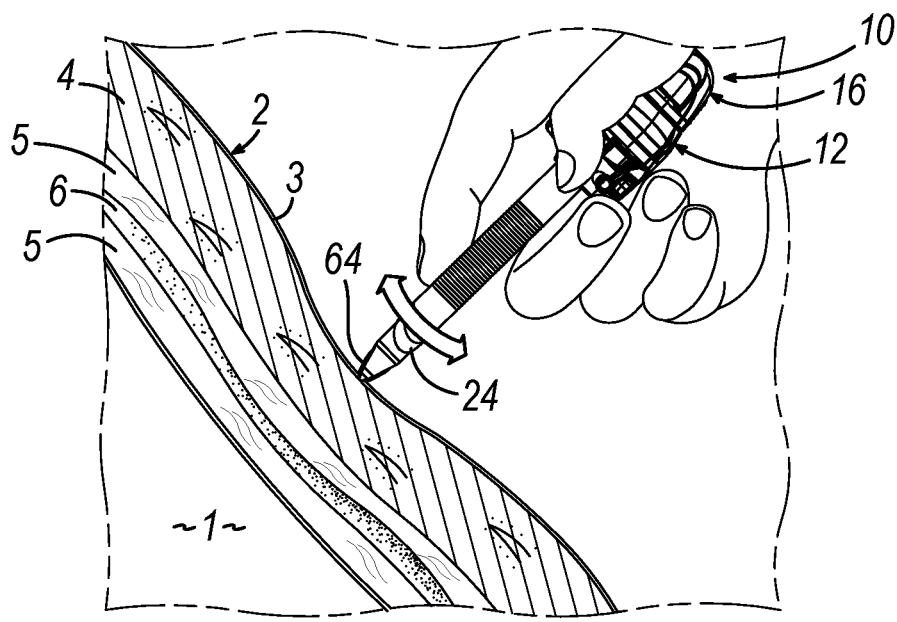
FIG. 3A depicts a side sectional view of the trocar of FIG. 1 being manipulated by a clinician through tissue layers of an abdominal wall.
Figure 3B:
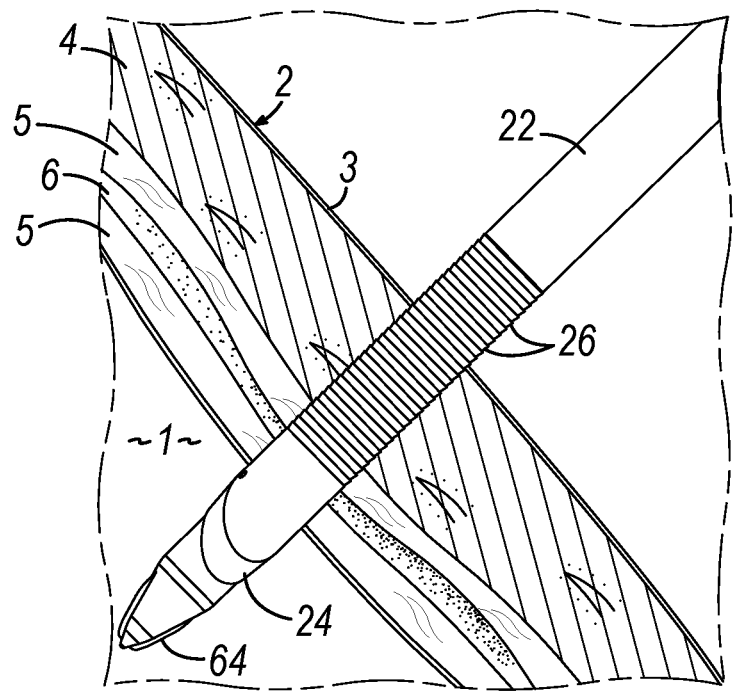
FIG. 3B depicts an enlarged side sectional view of the trocar of FIG. 1, showing a distal end of the trocar received within the abdominal cavity of FIG. 3A.
Figure 3C:
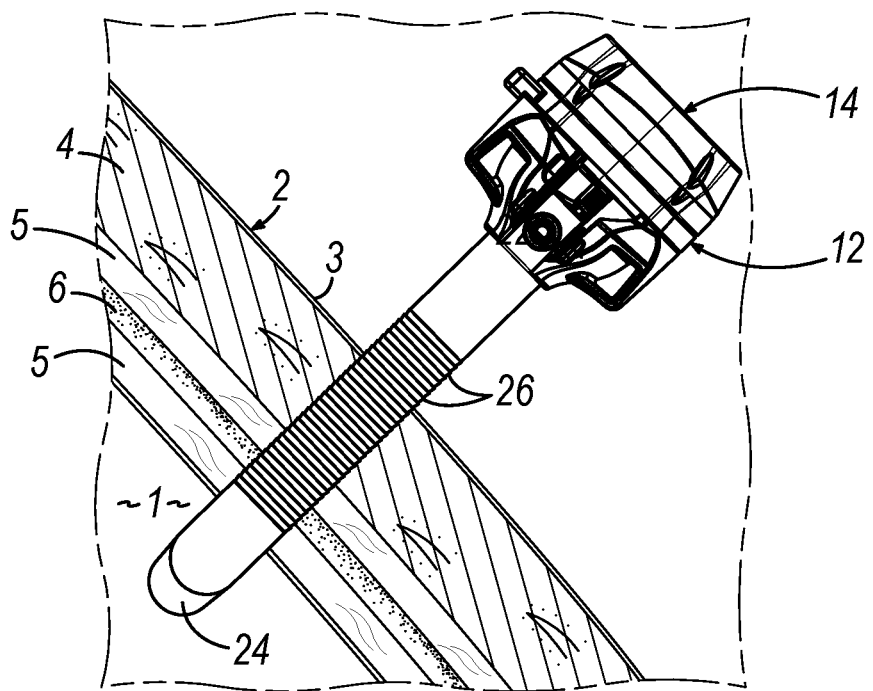
FIG. 3C depicts a side sectional view of the cannula assembly of FIG. 1, showing the cannula assembly remaining positioned within the abdominal wall of FIG. 3A following detachment and removal of the obturator.
Figure 3D:
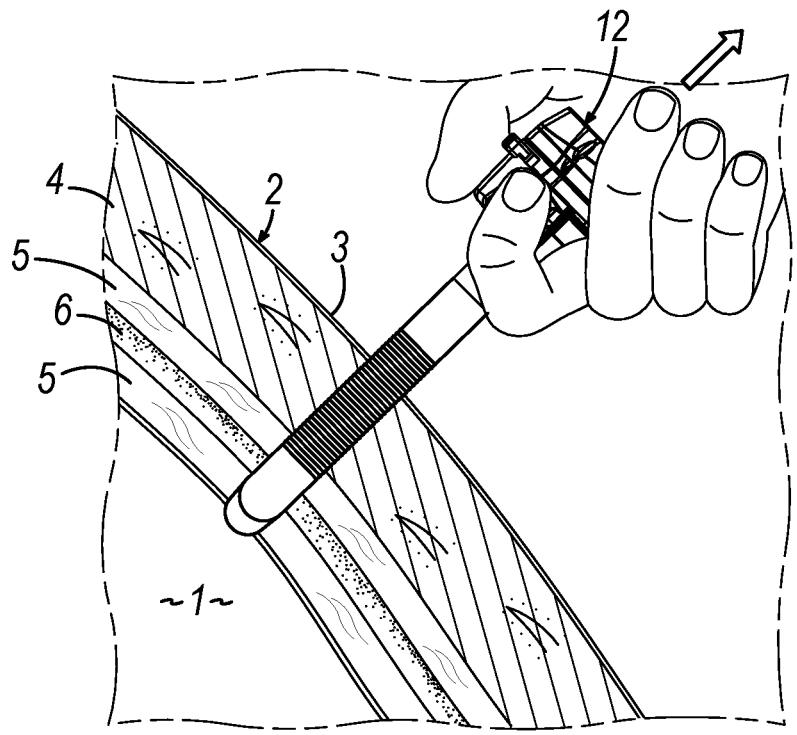
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
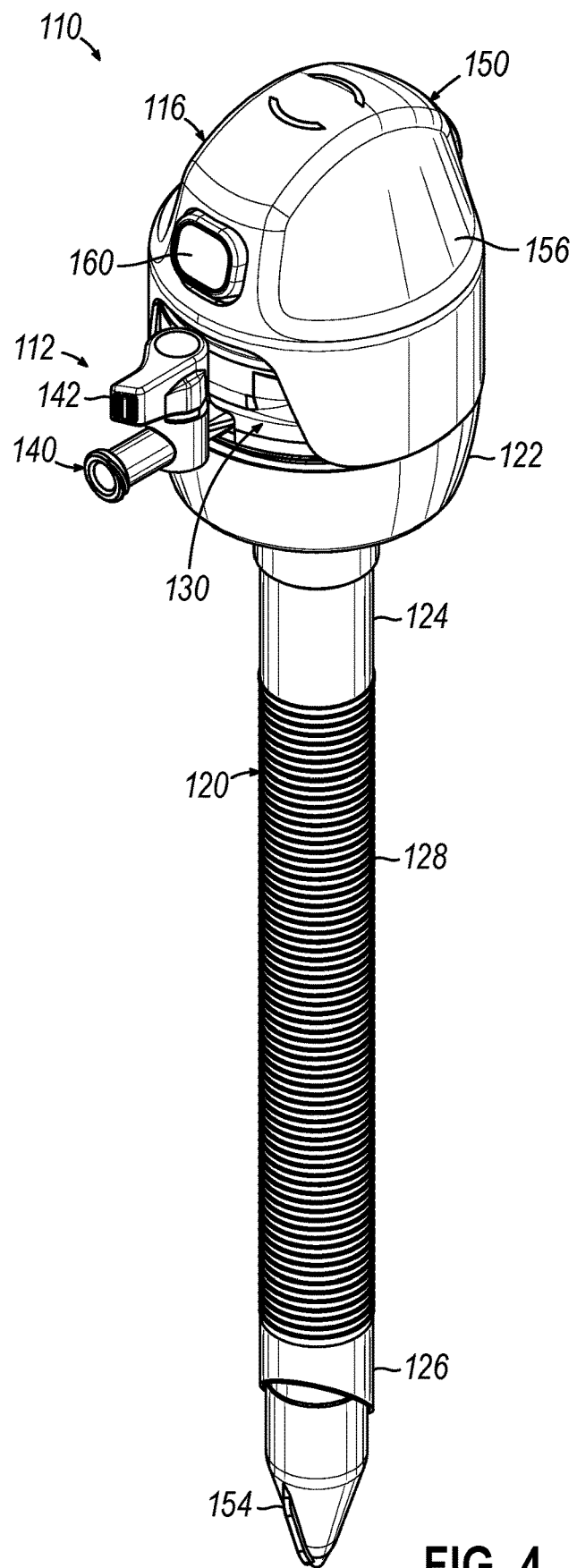
FIG. 4 depicts a perspective view of another exemplary trocar having a cannula assembly and an obturator shown in an assembled state.
Figure 5:
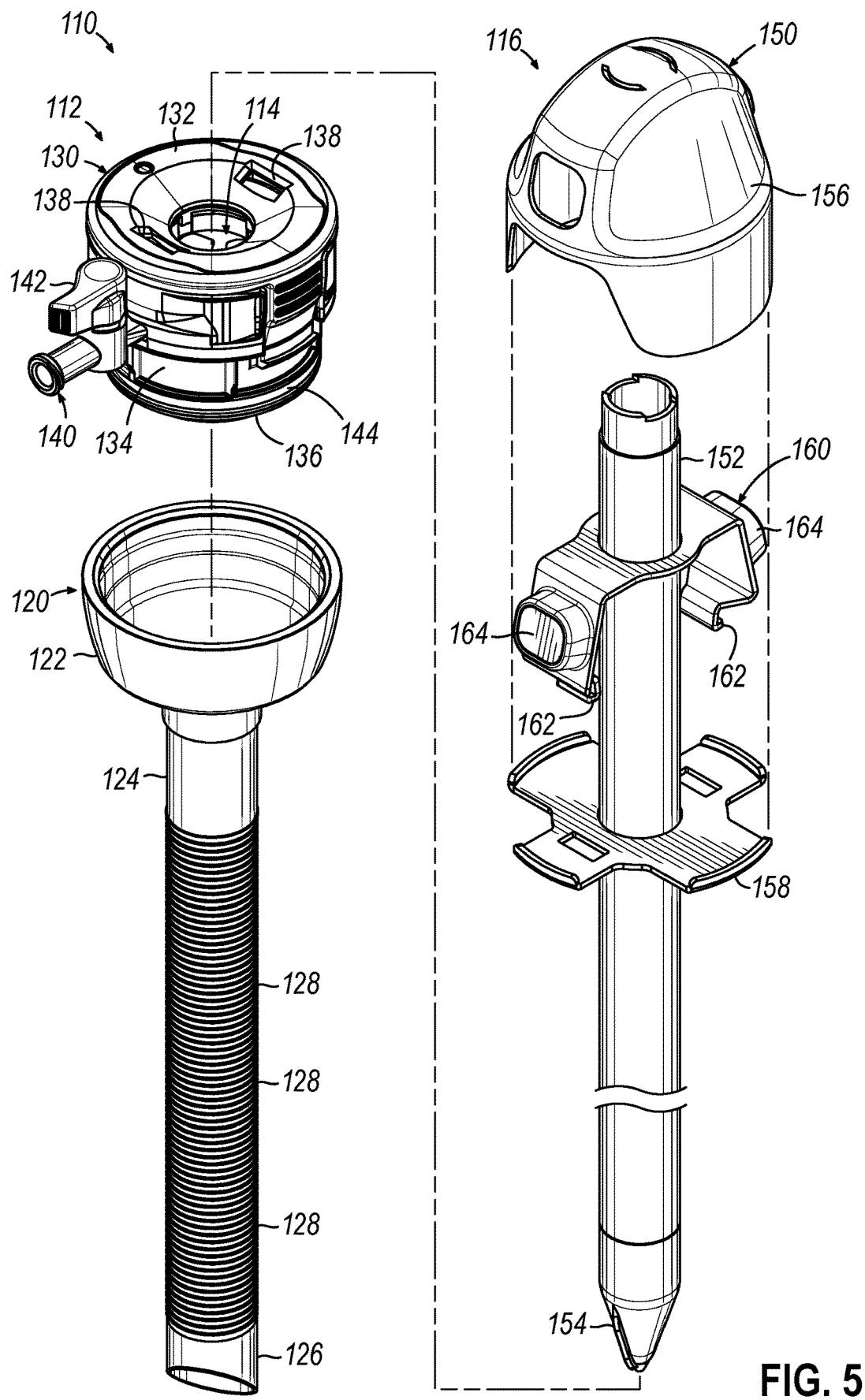
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Pinch-to-Clamp Depth Limiters

In some instances, a clinician may desire to limit the depth to which a single-use or reusable trocar (10, 110) may travel into abdominal wall (2) (e.g., after insertion of trocar (10, 110) to a desired position). Limiting the depth to which trocar (10, 110) may travel into abdominal wall (2) may assist in preventing distal tip (64, 154) of obturator (16, 116) and/or cannula tip (24, 126) of cannula assembly (12, 112) from inadvertently entering deeper than desired into abdominal cavity (1). Preventing over insertion of trocar (10, 110) may reduce undesirable contact of distal tip (64, 154) and/or cannula tip (24, 126) with anatomical structures contained within abdominal cavity (1). Preventing over insertion of trocar (10, 110) may also avoid inadvertently reducing the available surgical working space within abdominal cavity (1).

Alternatively or in addition to limiting the depth to which single-use or reusable trocar (10, 110) may travel into abdominal wall (2), the clinician may desire to stabilize trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tip (24, 126), and thus, the entry point of surgical instruments into abdominal cavity (1) in a desired position and/or orientation relative to abdominal cavity (1) such that surgical instruments may be easily directed distally through trocar (10, 110) at a selected working angle that is convenient for the clinician.

A. Exemplary Pinch-to-Clamp Depth Limiter with Living Hinge

Figure 6:
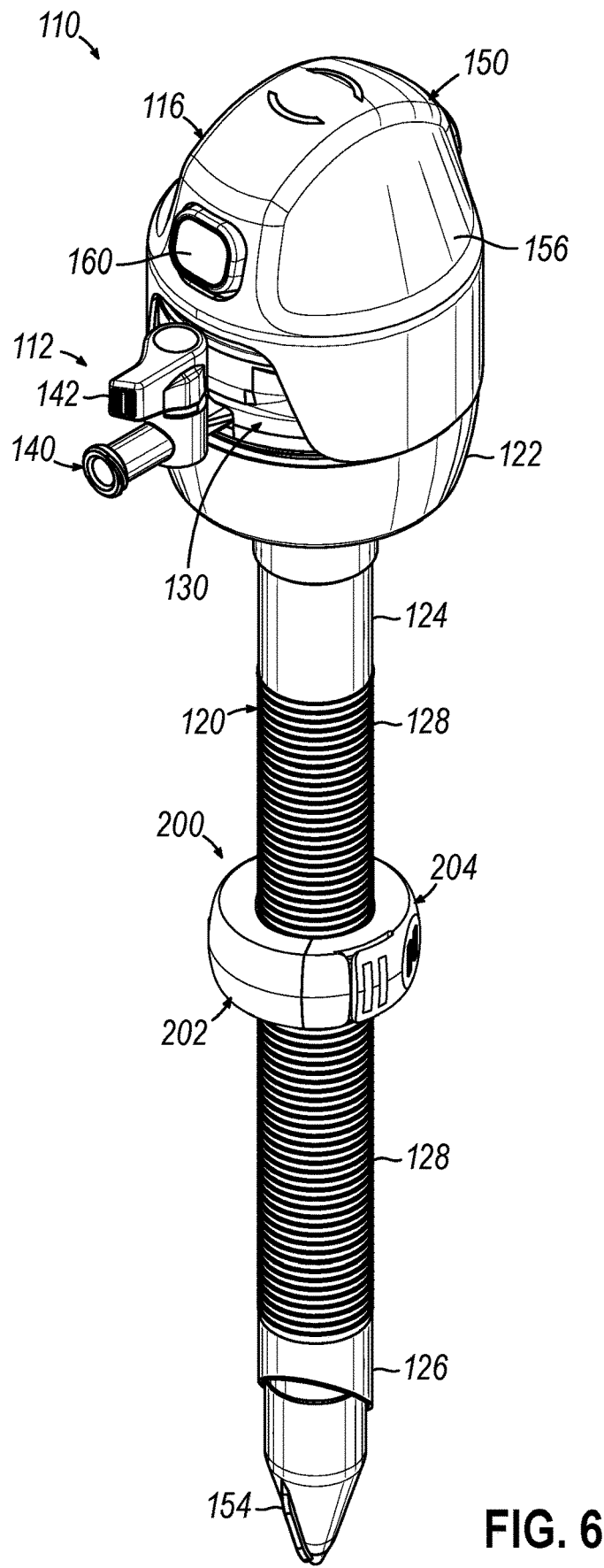
FIG. 6 depicts a perspective view of the trocar of FIG. 4, showing an exemplary depth limiter selectively clamped to the cannula tube of the trocar.

FIG. 6 shows a first exemplary depth limiter (200) selectively clamped to cannula tube (124) of second trocar (110). As described in greater detail below, depth limiter (200) may selectively limit the depth to which trocar (110) may travel distally into abdominal wall (2).

Figure 7:
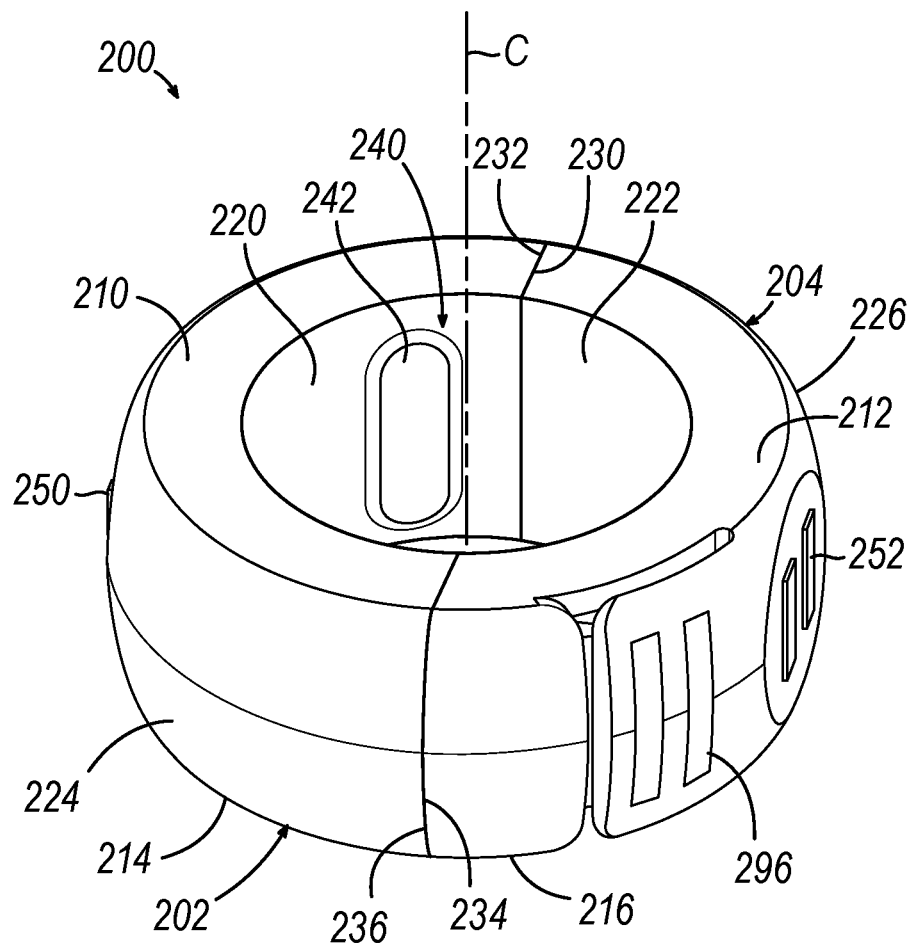
FIG. 7 depicts a perspective view of the depth limiter of FIG. 6.
Figure 8A:
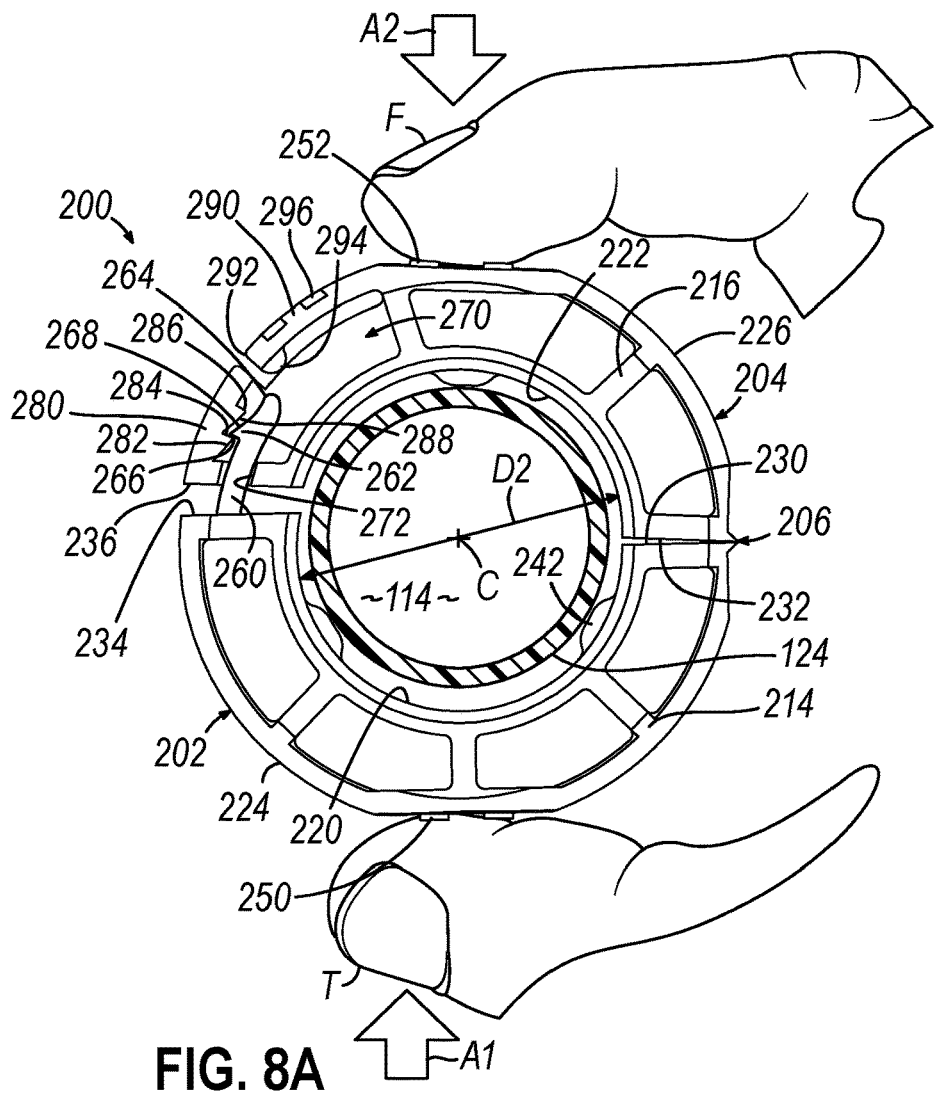
FIG. 8A depicts a bottom elevational view of the depth limiter of FIG. 6, showing the depth limiter in an open configuration, and further showing the depth limiter being pinched by a user to clamp the depth limiter onto the cannula tube of the trocar of FIG. 4.
Figure 8B:
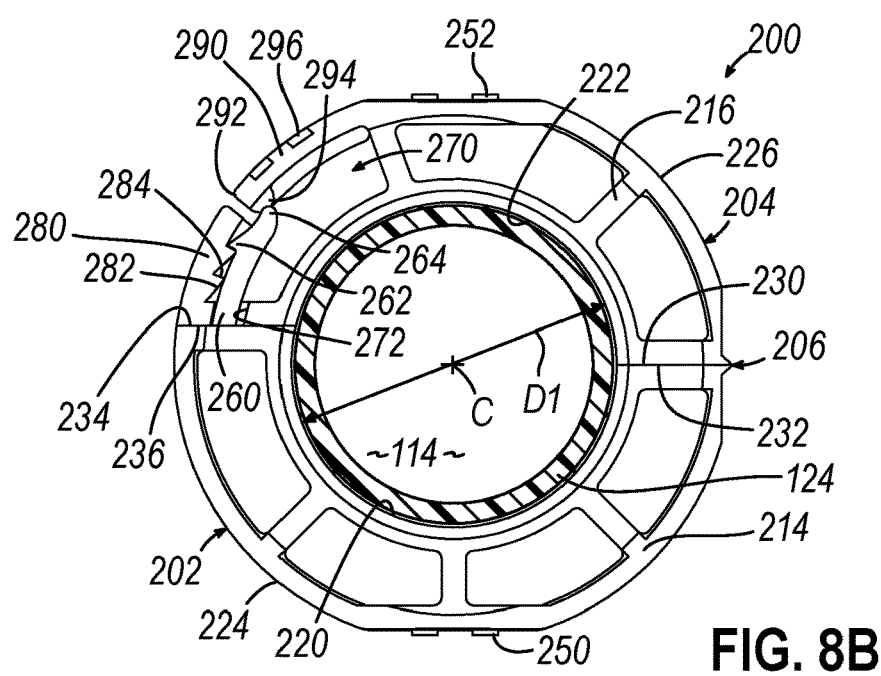
FIG. 8B depicts a bottom elevational view similar to FIG. 8A, showing the depth limiter of FIG. 6 in a clamped configuration such that the depth limiter is clamped onto the cannula tube of the trocar of FIG. 4.
Figure 8C:
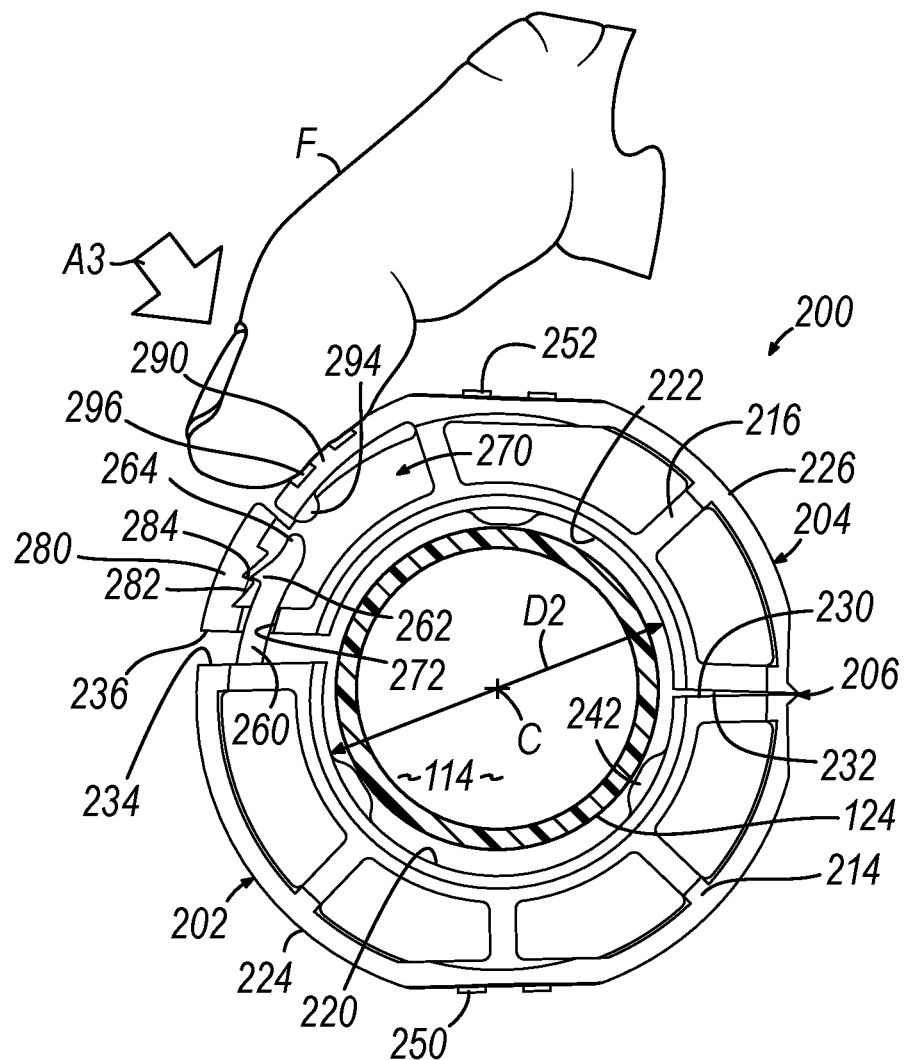
FIG. 8C depicts a bottom elevational view similar to FIG. 8B, showing a release button of the depth limiter of FIG. 6 being depressed by a user to allow unclamping of the depth limiter from the cannula tube of the trocar of FIG. 4.

As best shown in FIGS. 7-8C, depth limiter (200) includes first and second body portions (202, 204) pivotably coupled to each other by a hinge (206) such that first and second body portions (202, 204) are pivotable relative to each other between at least one open configuration (e.g., FIG. 8A) and at least one clamped configuration (e.g., FIG. 8B). In the example shown, first and second body portions (202, 204) and hinge (206) are integrally formed together as a unitary piece. For example, first and second body portions (202, 204) and hinge (206) may be molded together as a single component, such as from a polymeric material, including one or more plastics. Such a construction may allow depth limiter (200) to be considered a disposable unit, intended to be separated from cannula (120) and replaced after each procedure. For instance, such a construction may allow depth limiter (200) to be easily manufactured and sold at a price point that renders depth limiter (200) suitable for disposal after a single use, similar to trocar (10) and seal assembly (130) described above. In other versions, one or more portions of depth limiter (200) may be formed of surgical steel or other material suitable to render depth limiter sterilizable and reusable for multiple surgical procedures. In any event, the illustrated hinge (206) includes a thinned portion of the same material as first and second body portions (202, 204) such that first and second body portions (202, 204) are permitted to bend thereabout, such that hinge (206) may be considered a "living" hinge.

In the example shown, depth limiter (200) has a generally annular, ring-shaped profile when first and second body portions (202, 204) are in the clamped configuration, and has a generally split ring-shaped profile when first and second body portions (202, 204) are in the open configuration.

To this end, first and second body portions (202, 204) include first and second generally C-shaped proximal surfaces (210, 212), first and second generally C-shaped distal surfaces (214, 216), first and second generally semi-circular inner surfaces (220, 222), and first and second generally semi-circular outer surfaces (224, 226), respectively. Each body portion (202, 204) extends between a respective hinged end (230, 232) and a respective occluding end (234, 236), such that each body portion (202, 204) has a generally C-shaped profile. Hinge (206) is positioned between first and second hinged ends (230, 232) and at an interface between first and second outer surfaces (224, 226) such that first and second occluding ends (234, 236) are in contact or near-contact with each other when first and second body portions (202, 204) are in the clamped configuration; and such that first and second occluding ends (234, 236) are spaced apart from each other when first and second body portions (202, 204) are in the open configuration. In this manner, first and second inner surfaces (220, 222) collectively define an expandable cylindrical bore (240) extending longitudinally along a central axis (C) of depth limiter (200), and having a relatively constricted configuration when first and second body portions (202, 204) are in the clamped configuration, and having a relatively unconstricted configuration when first and second body portions (202, 204) are in the open configuration.

More particularly, and as shown in FIG. 8B, when first and second body portions (202, 204) are in the clamped configuration, first and second inner surfaces (220, 222) may collectively form a first effective cross dimension (D1) that extends diametrically and is sized to restrict axial movement of depth limiter (200) relative to cannula tube (124) of trocar (110), such as by generating an interference condition between cannula tube (124) and first and second inner surfaces (220, 222). On the other hand, and as shown in FIG. 8A, when first and second body portions (202, 204) are in the open configuration, first and second inner surfaces (220, 222) may collectively form a second effective cross dimension (D2) that extends diametrically and is sized to allow for axial movement of depth limiter (200) relative to cannula tube (124) of trocar (110), such as by allowing first and second inner surfaces (220, 222) to slide along cannula tube (124).

The illustrated first and second inner surfaces (220, 222) each include one or more tube gripping features in the form of radially inwardly extending ridges (242) arranged circumferentially thereabout. Ridges (242) are configured to grip an outer surface of cannula tube (124), such as ribs (128), when first and second body portions (202, 204) are in the clamped configuration, and thereby assist in restricting axial movement of depth limiter (200) relative to cannula tube (124). More specifically, ridges (242) of the present example extend substantially between the respective proximal surface (210, 212) and distal surface (214, 216) of the respective body portions (202, 204) such that each ridge (242) may extend across and grip a plurality of ribs (128). It will be appreciated, however, that first and second inner surfaces (220, 222) may be provided with various other types of tube gripping features in other versions of depth limiter (200). In one example, tube gripping features may be omitted such that first and second inner surfaces (220, 222) directly grip cannula tube (124) when first and second body portions (202, 204) are in the clamped configuration.

The illustrated first and second outer surfaces (224, 226) include diametrically opposed first and second finger grips (250, 252), respectively, positioned generally centrally between the respective hinged end (230, 232) and occluding end (234, 236). First and second finger grips (250, 252) are configured to provide a visual and/or tactile indication to a user of the locations on first and second body portions (202, 204), respectively, to be squeezed or pinched toward each other for effectively and ergonomically moving first and second body portions (202, 204) toward the clamped configuration.

As shown in FIGS. 8A-8C, depth limiter (200) also includes a first locking member in the form of a ratcheting post or pawl (260) circumferentially extending from first occluding end (234) of first body portion (202) toward second occluding end (236) of second body portion (204). In the example shown, pawl (260) includes a radially outwardly-directed pawl tooth (262) and terminates in a release tab (264). Pawl tooth (262) includes a relatively steep locking surface (266) generally facing toward first occluding end (234) and a relatively shallow camming surface (268) generally facing away from first occluding end (234). In the example shown, pawl (260) extends into an interior cavity (270) of second body portion (204) via an aperture (272) provided in second occluding end (236). As described in greater detail below, pawl (260) is resiliently biased radially outwardly relative to central axis (C).

Depth limiter (200) further includes a second locking member in the form of a circumferentially-extending ratchet catch or rack (280) positioned within the second body portion (204) and including a series of alternating radially inwardly-directed rack teeth (282) and rack recesses (284). Rack teeth (282) each include a relatively steep locking surface (286) generally facing away from second occluding end (236) and a relatively shallow camming surface (288) generally facing toward second occluding end (236). Each rack recess (284) is sized and configured to receive pawl tooth (262) when aligned therewith.

In the example shown, camming surface (288) of each rack tooth (282) is configured to engage camming surface (268) of pawl tooth (262) to allow movement of first and second body portions (202, 204) from the open configuration toward the clamped configuration, such as when first and second finger grips (250, 252) are squeezed or pinched toward each other as shown in FIG. 8A. More particularly, camming surface (288) of each rack tooth (282) is configured to at least partially redirect camming surface (268) of pawl tooth (262) by overcoming the radial outward biasing of pawl tooth (262) to urge pawl tooth (262) radially inwardly. This interaction enables pawl tooth (262) to advance along rack teeth (282) and thus allows pawl (260) to advance further into interior cavity (270) (e.g., in a clockwise direction based on the frame of reference in FIG. 8A) such that first and second occluding ends (234, 236) are permitted to pivot toward each other about hinge (206). In this manner, pawl (260) and rack (280) may cooperate to allow approximation of first and second body portions (202, 204) toward the clamped configuration.

Conversely, locking surface (286) of each rack tooth (282) is configured to engage locking surface (266) of pawl tooth (262) to prevent and/or arrest movement of first and second body portions (202, 204) toward the open configuration as shown in FIG. 8B. More particularly, locking surface (286) of each rack tooth (282) is configured to catch or abut locking surface (266) of pawl tooth (262) when the radial outward biasing of pawl tooth (262) urges pawl tooth (262) into the corresponding rack recess (284) to securely seat pawl tooth (262) within rack recess (284). Accordingly, pawl tooth (262) is prevented from retracting along rack teeth (282) and thus pawl (260) is prevented from withdrawing from interior cavity (270) (e.g., in a counterclockwise direction based on the frame of reference in FIG. 8B) such that first and second occluding ends (234, 236) are inhibited from pivoting away from each other about hinge (206). In this manner, pawl (260) and rack (280) may cooperate to prevent and/or arrest movement of first and second body portions (202, 204) toward the open configuration. In the example shown, at least one rack recess (284) is positioned to receive pawl tooth (262) when first and second body portions (202, 204) are in the clamped configuration with first and second occluding ends (234, 236) in contact or near-contact with each other. Thus, when first and second body portions (202, 204) are in the clamped configuration, pawl (260) and rack (280) may cooperate to selectively lock first and second body portions (202, 204) in the clamped configuration. It will be appreciated, however, that depth limiter (200) may be provided with various other types of locking members in other versions of depth limiter (200).

Depth limiter (200) of the present version also includes an unlocking member in the form of a release button (290) provided in a localized region of second body portion (204) proximate to rack (280). Release button (290) includes a flexible cantilevered overhang or flange (292) contiguous with second outer surface (226), a radially inwardly-directed protrusion (294) positioned at or near a terminal end of flange (292), and a third finger grip (296) positioned on second outer surface (226) along flange (292). Flange (292) may be biased toward the configuration shown in FIGS. 8A and 8B and may be flexible in at least a radially inward direction to the configuration shown in FIG. 8C such that protrusion (294) may be selectively moved radially inwardly toward release tab (264) of pawl (260) as described in greater detail below.

In the example shown, protrusion (294) of release button (290) is configured to selectively engage release tab (264) of pawl (260) to allow movement of first and second body portions (202, 204) from the clamped configuration toward the open configuration as shown in FIG. 8C. More particularly, protrusion (294) of release button (290) is configured to selectively release pawl tooth (262) from at least one rack recess (284) when flange (292) is depressed radially inwardly by overcoming the radial outward biasing of release tab (264) to urge release tab (264) together with pawl tooth (262) radially inwardly. As a result, locking surface (266) of pawl tooth (262) is disengaged from the corresponding locking surface (286) of rack tooth (282), which allows pawl tooth (262) to at least partially retract along rack teeth (282) and thus allowing pawl (260) to at least partially withdraw from interior cavity (270) (e.g., in a counterclockwise direction based on the frame of reference in FIG. 8C) such that first and second occluding surfaces (234, 236) are permitted to pivot away from each other about hinge (206). Third finger grip (296) is configured to provide a visual and/or tactile indication to a user of the location on second body portion (204) to be depressed radially inwardly for effectively and ergonomically moving protrusion (294) toward release tab (264) of pawl (260) for releasing pawl tooth (262) from rack recess (284). In this manner, release button (290) and pawl (260) may cooperate to selectively allow movement of first and second body portions (202, 204) from the clamped configuration toward the open configuration. It will be appreciated, however, that depth limiter (200) may be provided with various other types of unlocking members in other versions of depth limiter (200).

In some examples, first and second body portions (202, 204) may be biased toward the open configuration. For example, first and second occluding ends (234, 236) may be resiliently biased away from each other, such as via a torsion spring member (not shown) incorporated into hinge (206) or an external spring member (not shown) positioned directly between first and second occluding ends (234, 236). In other examples, hinge (206) may be constructed as a living hinge having a shape and thickness suitable to impart opposing resilient bias on body portions (202, 204) at their hinged ends (230, 232). In this manner, first and second body portions (202, 204) may be configured to automatically move from the clamped configuration toward the open configuration in response to pawl tooth (262) being released from rack recess (284). In addition or alternatively, first and second body portions (202, 204) may be configured to be gripped by a user and manually moved toward the open configuration when pawl tooth (262) is released from rack recess (284).

During operation, and with continuing reference to FIGS. 8A-8C, depth limiter (200) may be initially positioned about cannula tube (124) of trocar (110) such that cannula tube (124) is received within expandable bore (240) prior to deployment of trocar (110) into the patient's abdominal cavity (1). In one example, central axis (C) of depth limiter (200) may coincide with a central axis (not shown) of trocar (110). During deployment of trocar (110) into abdominal cavity (1), first and second body portions (202, 204) may be in either the open configuration or the clamped configuration, as may be desired.

In some cases, the clinician may desire to allow axial movement of depth limiter (200) relative to cannula tube (124) of trocar (110) during deployment. Thus, the clinician may choose to maintain first and second body portions (202, 204) in the open configuration. By maintaining first and second body portions (202, 204) in the open configuration, cannula tube (124) may be unconstricted by expandable bore (240). More particularly, first and second inner surfaces (220, 222) may collectively form second effective cross dimension (D2) to allow axial movement of depth limiter (200) relative to cannula tube (124) of trocar (110), as shown in FIG. 8A.

In other cases, the clinician may desire to restrict axial movement of depth limiter (200) relative to cannula tube (124) of trocar (110) during deployment. For example, the clinician may desire to position depth limiter (200) at a predetermined axial location along cannula tube (124) corresponding to a desired depth of insertion of cannula (120) within cavity (1). Thus, the clinician may choose to move first and second body portions (202, 204) from the open configuration toward the clamped configuration. To this end, the clinician may squeeze or pinch first and second finger grips (250, 252) toward each other via the clinician's thumb (T) and finger (F) as indicated by first and second arrows (A1, A2), respectively, in FIG. 8A to effectively and ergonomically move first and second body portions (202, 204) toward the clamped configuration. By moving first and second body portions (202, 204) toward the clamped configuration, cannula tube (124) may be constricted by expandable bore (240). More particularly, first and second inner surfaces (220, 222) may collectively form first effective cross dimension (D1) to restrict axial movement of depth limiter (200) relative to cannula tube (124) of trocar (110), as shown in FIG. 8B. Ridges (242) may grip an outer surface of cannula tube (124) to assist in restricting axial movement of depth limiter relative to cannula tube (124). The movement of first and second body portions (202, 204) toward the clamped configuration may be permitted by the cooperation of pawl (260) and rack (280) described above. Once first and second body portions (202, 204) have reached the closed configuration, pawl (260) and rack (280) may cooperate to selectively lock first and second body portions (202, 204) in the clamped configuration as described above such that depth limiter (200) may apply a continuous clamping pressure to cannula tube (124). Thus, the clinician may release first and second finger grips (250, 252) while depth limiter (200) remains reliably clamped to cannula tube (124).

With depth limiter (200) positioned about cannula tube (124) in either an axially restricted or unrestricted state, the clinician may deploy trocar (110) into the patient's abdominal cavity (1) as described above with respect to FIGS. 3A and 3B to position cannula (120) at a desired depth of insertion in cavity (1). In cases where depth limiter (200) is clamped to cannula tube (124) during deployment at a predetermined axial location along cannula tube (124) corresponding to a desired depth of insertion of cannula (120) within cavity (1), contact between distal surfaces (214, 216) of depth limiter (200) and abdominal wall (2) may provide a visual and/or tactile indication to the clinician that cannula (120) has reached the desired depth of insertion in cavity (1). In this manner, depth limiter (200) may assist in preventing distal tip (154) of obturator (116) and/or cannula tip (126) of cannula assembly (112) from inadvertently entering deeper than desired into abdominal cavity (1) during deployment. In other cases, depth limiter (200) may be clamped to cannula tube (124) after cannula (120) is positioned at a desired depth of insertion in cavity (1).

In some cases, it may be desirable to adjust the axial location of depth limiter (200) along cannula tube (124) after depth limiter (200) has already been clamped to cannula tube (124). Thus, the clinician may choose to move first and second body portions (202, 204) from the clamped configuration toward the open configuration. To this end, the clinician may depress third finger rest (296) radially inwardly via the clinician's finger (F) as indicated by third arrow (A3) in FIG. 8C to effectively and ergonomically move protrusion (294) toward release tab (264) of pawl (260) and thereby release pawl tooth (262) from rack recess (284) such that movement of first and second body portions (202, 204) from the clamped configuration toward the open configuration may be permitted, as described above. By moving first and second body portions (202, 204) toward the open configuration, cannula tube (124) may be unconstricted by expandable bore (240). More particularly, first and second inner surfaces (220, 222) may collectively form second effective cross dimension (D2) to allow axial movement of depth limiter (200) relative to cannula tube (124) of trocar (110), as shown in FIG. 8C. Thus, the clinician may adjust the axial location of depth limiter (200) along cannula tube (124), and may subsequently re-clamp depth limiter (200) onto cannula tube (124) as described above with reference to FIGS. 8A and 8B.

Depth limiter (200) may remain clamped onto cannula tube (124) during performance of the laparoscopic surgical procedure with first and second distal surfaces (214, 216) of depth limiter (200) resting against abdominal wall (2). In this manner, depth limiter (200) may assist in preventing cannula tip (126) of cannula assembly (112) from inadvertently entering deeper than desired into abdominal cavity (1) during performance of the laparoscopic surgical procedure.

Upon completion of the laparoscopic surgical procedure, depth limiter (200) may be withdrawn proximally from abdominal wall (2) together with cannula assembly (112). Depth limiter (200) may be unclamped from cannula tube (124) by moving first and second body portions (202, 204) toward the open configuration as described above with reference to FIG. 8C. In one example, depth limiter (200) may be simply disposed of after completion of a single laparoscopic surgical procedure.

B. Exemplary Pinch-to-Clamp Depth Limiter with Clasp Mechanism

Figure 9:
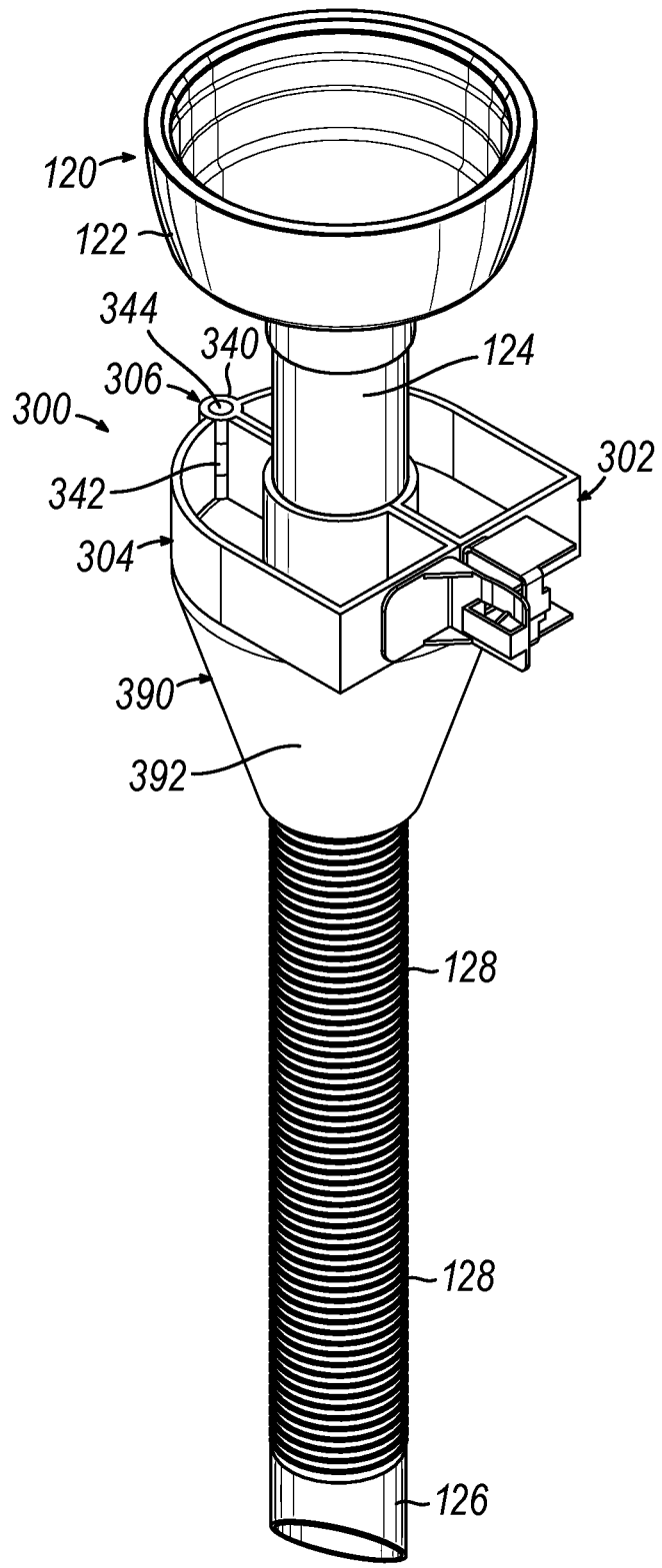
FIG. 9 depicts a perspective view of the cannula of the trocar of FIG. 4, showing another exemplary depth limiter selectively clamped to the cannula tube.
Figure 10:
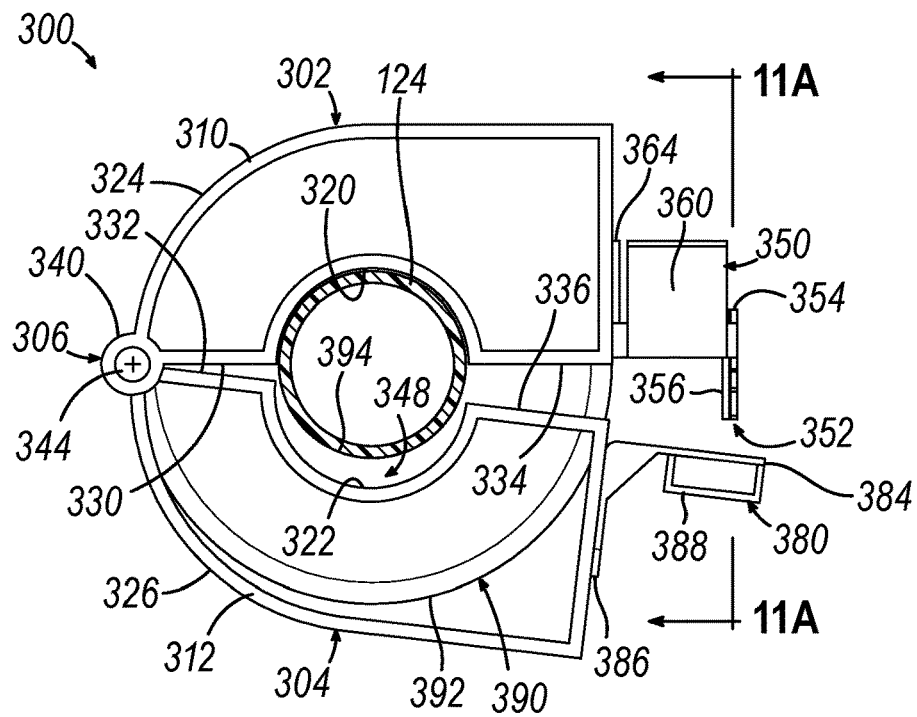
FIG. 10 depicts a top elevational view of the depth limiter of FIG. 9, showing the depth limiter in an open configuration and positioned about the cannula tube of the trocar of FIG. 4.
Figure 11A:
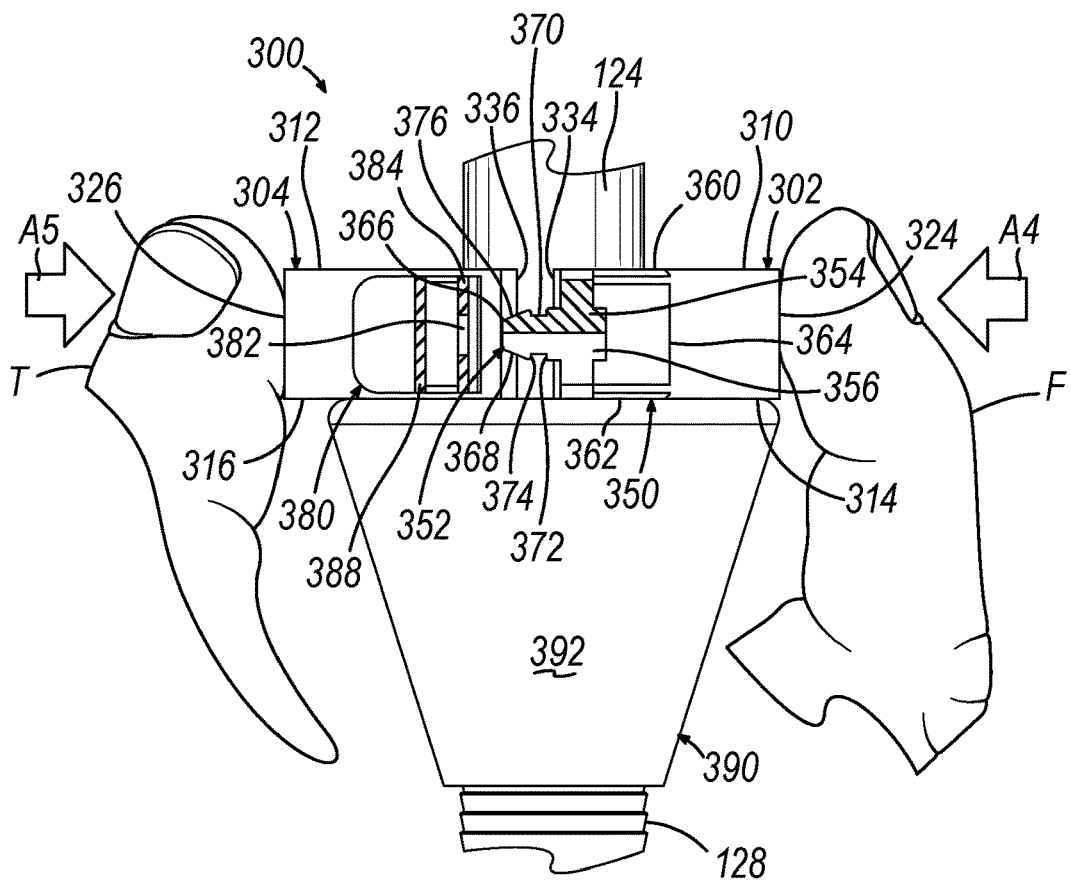
FIG. 11A depicts a cross sectional view of the depth limiter of FIG. 9, taken along section line 11A-11A in FIG. 10, showing the depth limiter being pinched by a user to clamp the depth limiter onto the cannula tube of the trocar of FIG. 4.
Figure 11B:
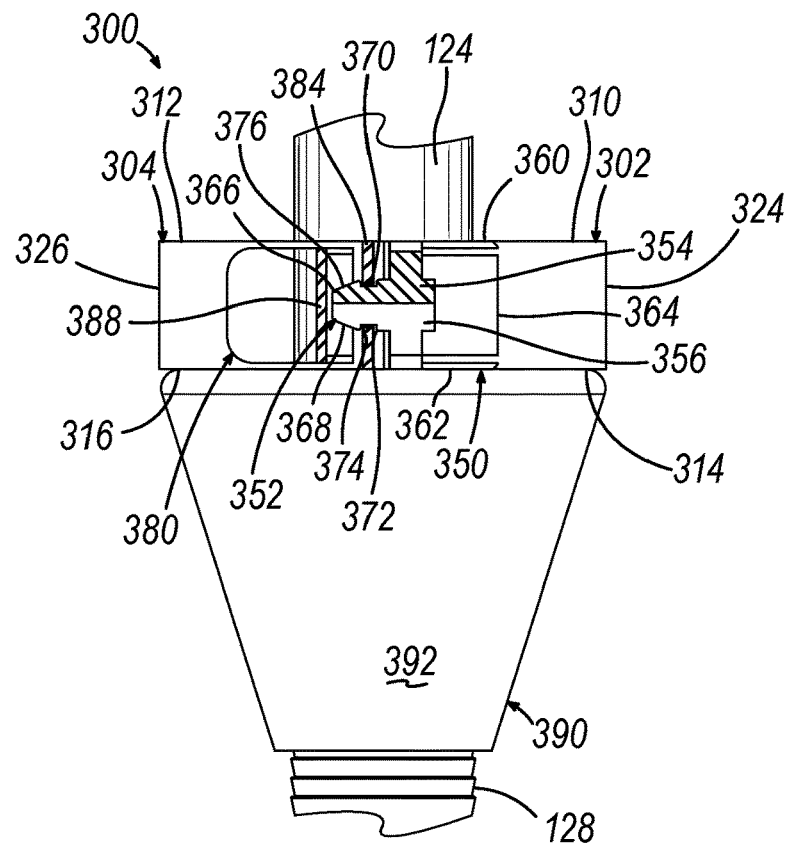
FIG. 11B depicts a cross sectional view similar to FIG. 11A, showing the depth limiter of FIG. 9 in a clamped configuration such that the depth limiter is clamped onto the cannula tube of the trocar of FIG. 4.

In some instances, it may be desirable to provide a cannula depth limiter with a closure mechanism that differs from the pawl-rack mechanism (260, 280) of depth limiter (200) described above. FIG. 9 shows a second exemplary depth limiter (300) selectively clamped to cannula tube (124) of second trocar (110). Similar to depth limiter (200), depth limiter (300) may selectively limit the depth to which trocar (110) may travel distally into abdominal wall (2). As best shown in FIGS. 10-11B, depth limiter (300) includes first and second body portions (302, 304) coupled to each other by a hinge (306) and pivotable between an open configuration (e.g., FIGS. 10 and 11A) and a clamped configuration (e.g., FIG. 11B).

First and second body portions (302, 304) include first and second proximal surfaces (310, 312), first and second distal surfaces (314, 316), first and second inner surfaces (320, 322), first and second outer surfaces (324, 326), first and second hinged ends (330, 332), and first and second occluding ends (334, 336), respectively. First and second body portions (302, 304) further include first and second knuckles (340, 342) which together with a pin (344) collectively define hinge (306). First and second inner surfaces (320, 322) collectively define an expandable cylindrical bore (348).

Depth limiter (300) includes a male clasp (350) including an axially compressible flared post (352) having proximal and distal post portions (354, 356) generally parallel to and overlapping each other in a radial direction, and flexibly coupled to first outer surface (324) via respective proximal and distal sidewalls (360, 362) and a base wall (364). Proximal and distal sidewalls (360, 362) may be resiliently biased toward the configuration shown, wherein flared post (352) may have a first effective height, and may be flexible in at least an axially inward direction such that proximal and distal post portions (354, 356) may be moved axially inwardly toward each other to provide a second effective height of flared post (352). Proximal and distal post portions (354, 356) include proximal and distal post teeth (366, 368), respectively, and proximal and distal recesses (370, 372), respectively. Post teeth (366, 368) each include a locking surface (374) and a camming surface (376).

Depth limiter (300) further includes a female clasp (380) including an aperture (382) provided in a sidewall (384) of female clasp (380) which is fixedly coupled to second outer surface (326) via a base wall (386). Aperture (382) is sized and configured to selectively restrict the passage of flared post (352) therethrough when flared post (352) has the first effective height and to selectively allow the passage of flared post (352) therethrough when flared post (352) has the second effective height. A stop ribbon (388) is positioned behind aperture (382) relative to male clasp (350).

A peripheral edge of aperture (382) is configured to at least partially redirect camming surfaces (376) of post teeth (366, 368) to urge post teeth (366, 368) axially inwardly, such as when diametrically opposed locations on first and second body portions (302, 304) are squeezed or pinched toward each other via the clinician's finger (F) and thumb (T) as indicated by fourth and fifth arrows (A4, A5), respectively, in FIG. 11A. As a result, the effective height of flared post (352) may be reduced from the first effective height to the second effective height such that post teeth (366, 368) are permitted to advance through aperture (382). Peripheral edge of aperture (382) is configured to catch or abut locking surfaces (374) of post teeth (366, 368) when the axial outward biasing of post teeth (366, 368) urges the corresponding recesses (370, 372) into engagement with peripheral edge of aperture (382), thereby preventing flared post (352) from withdrawing from aperture (382). Proximal and distal sidewalls (360, 362) are configured to be pinched or squeezed toward each other to selectively urge post teeth (366, 368) axially inwardly, thereby reducing the effective height of flared post (352) from the first effective height to the second effective height and allowing post teeth (366, 368) to retract through aperture (382).

Depth limiter (300) also includes a plug or spacer (390) positioned distally relative to first and second body portions (302, 304) and including a frustoconical body (392) and a cylindrical bore (394) configured to slidably receive cannula tube (124) of trocar (110). Spacer (390) is configured to be positioned about cannula tube (124) between distal surfaces (314, 316) and abdominal wall (2) to prevent hinge (306) from inadvertently pinching abdominal wall (2) during pivoting of first and second body portions (302, 304) toward or away from each other. In one example, each of first and second body portions (302, 304), male and female clasps (350, 380), and spacer (390) may be separately formed as individual pieces, such as from one or more plastic or metal materials.

C. Third Exemplary Depth Limiter

Figure 12:
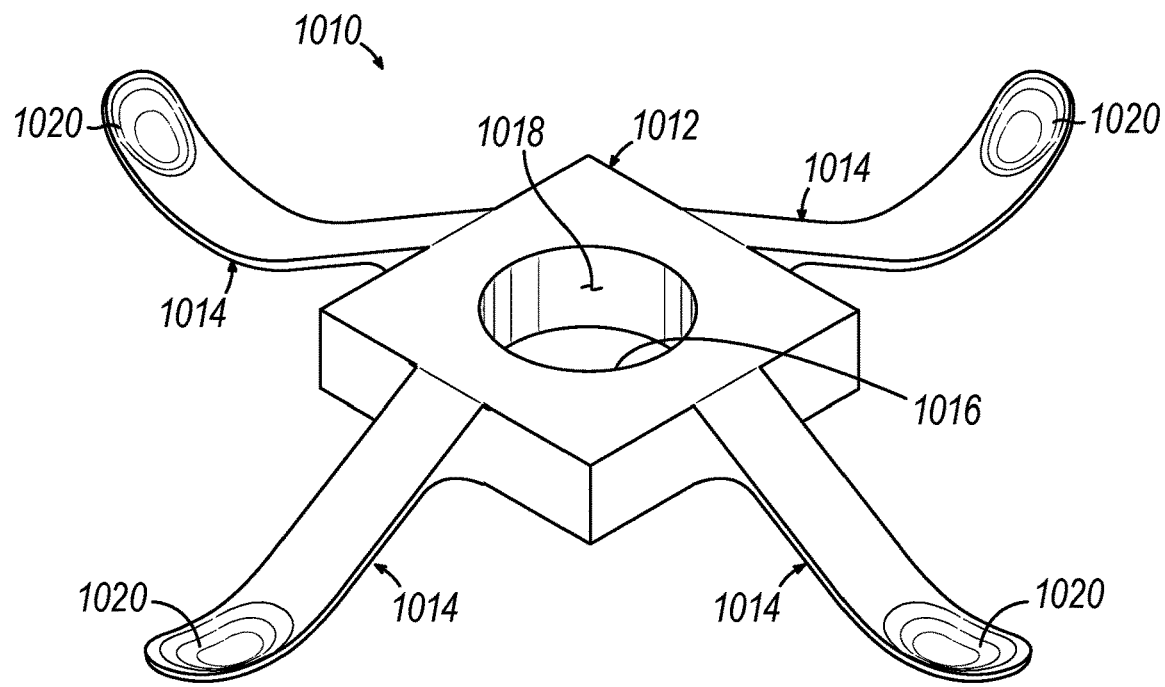
FIG. 12 depicts a perspective view of another exemplary depth limiter that includes four legs.

FIG. 12 shows a perspective view of a third exemplary depth limiter (1010). Depth limiter (1010) includes a hub (1012) and a plurality of legs (1014). Depth limiter (1010) may be used in combination with depth limiters (200, 300) described above. While hub (1012) is shown as being generally square shaped, other shapes of hub (1012) are also envisioned. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). While FIGS. 12-13B describe depth limiter (1010) with reference to cannula tube (22) of trocar (10) of FIG. 1, other cannula tubes (e.g., cannula tube (124)) may also be used. Gripping surface (1018) may be smooth or non-smooth. As shown in FIG. 12, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped portions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10). This stabilization may be achieved using mechanical spring effects of each leg (1014). Legs (1014) may have a reduced mass allowing legs (1014) to flex outwardly, causing a variable amount of spring-resistance in each direction trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (20).

Figure 13A:
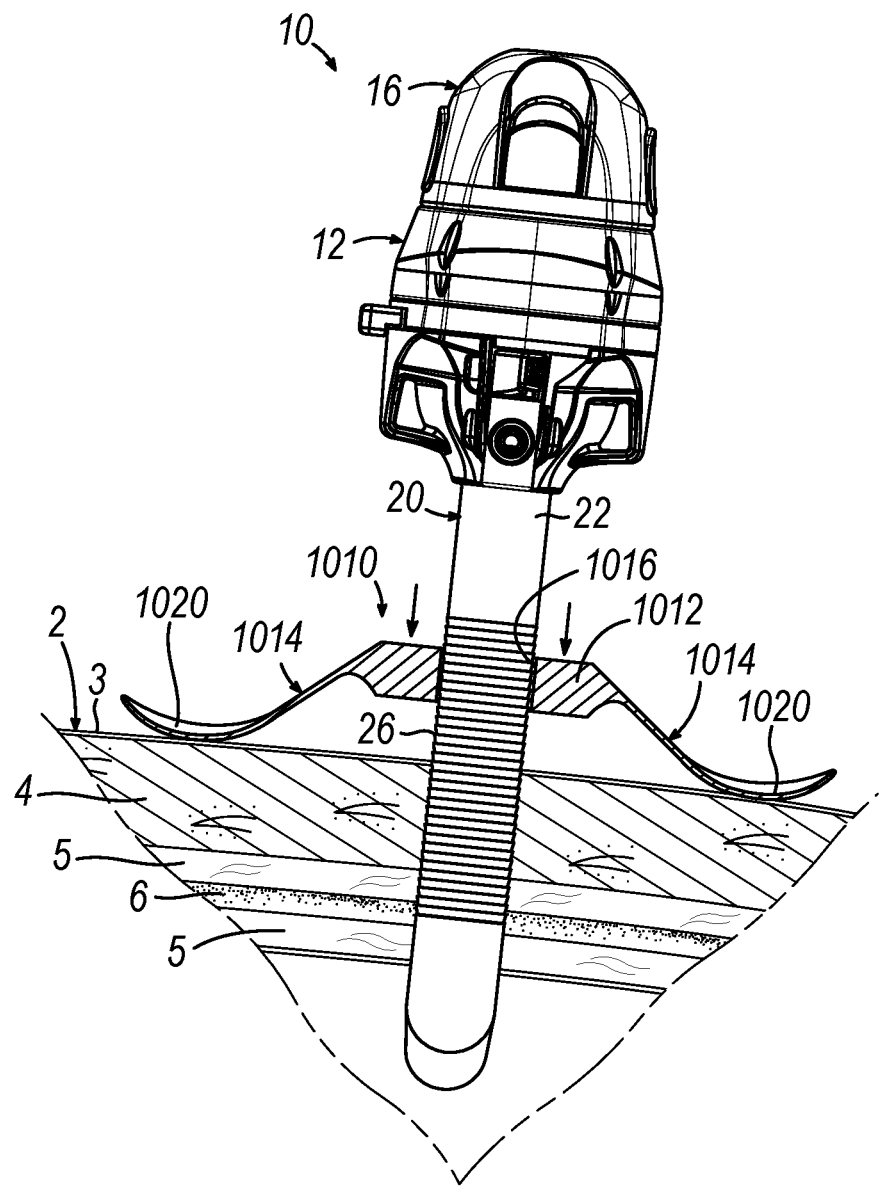
FIG. 13A depicts a partial side sectional view of the depth limiter of FIG. 12 coupled with the cannula tube of the cannula assembly of the trocar of FIG. 1, where the legs of the depth limiter are in a non-deployed configuration when the distal end of the trocar received within the abdominal cavity.
Figure 13B:
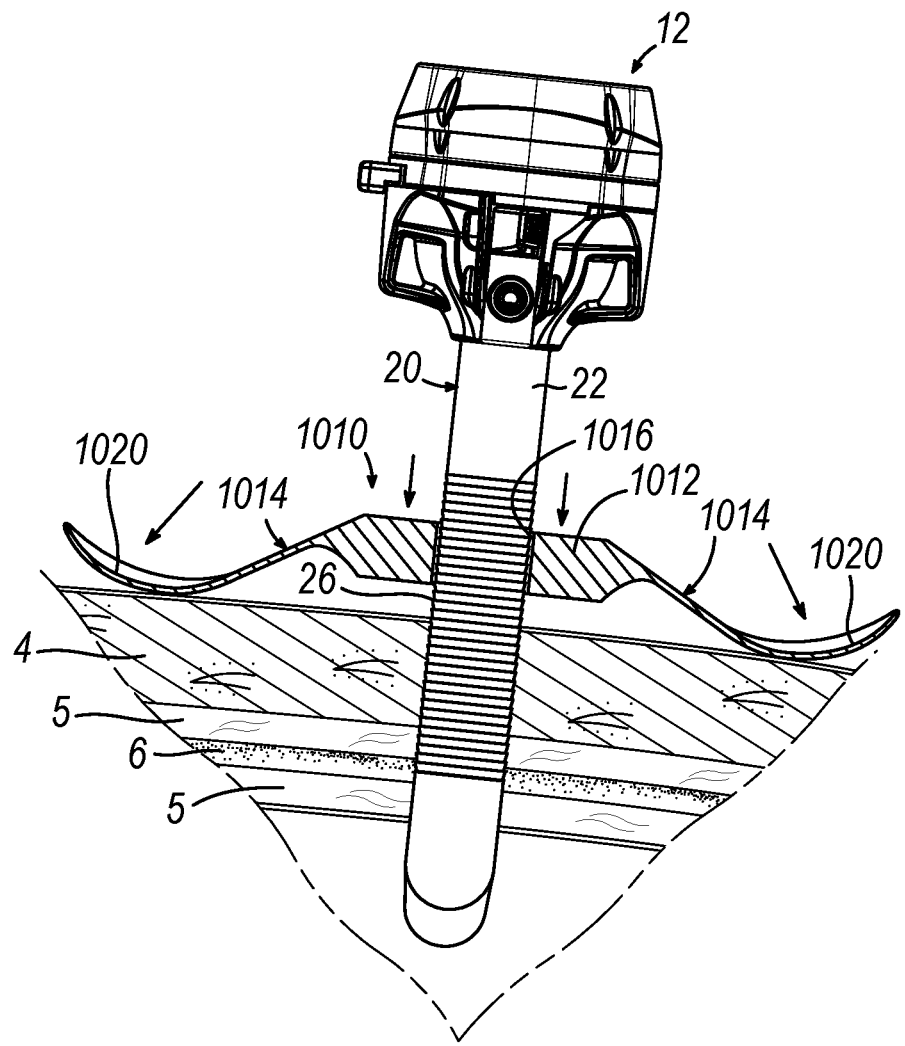
FIG. 13B depicts a partial side sectional view of the depth limiter of FIG. 12 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 13A-13B show depth limiter (1010); however, the teachings of FIGS. 13A-13B may also apply to depth limiters (1110, 1210) described in detail below. FIG. 13A shows a partial side sectional view of depth limiter (1010) of FIG. 12 coupled with cannula tube (22) of cannula assembly (12) of trocar (10) of FIG. 1, where legs (1014) of depth limiter (1010) are in a non-deployed configuration when distal end of trocar (10) received within abdominal cavity (1). In the non-deployed configuration (e.g., the resting configuration) of FIG. 13A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 13B shows a partial side sectional view of depth limiter (1010) of FIG. 12 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10)) may achieve, and may also reduce the velocity that trocar (10) may achieve that tilt (i.e., preventing sudden accidental moves within the body). To completely undeploy depth limiter (1010) from cannula tube (22), the user may retract cannula (20) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

D. Fourth Exemplary Depth Limiter

Figure 14:
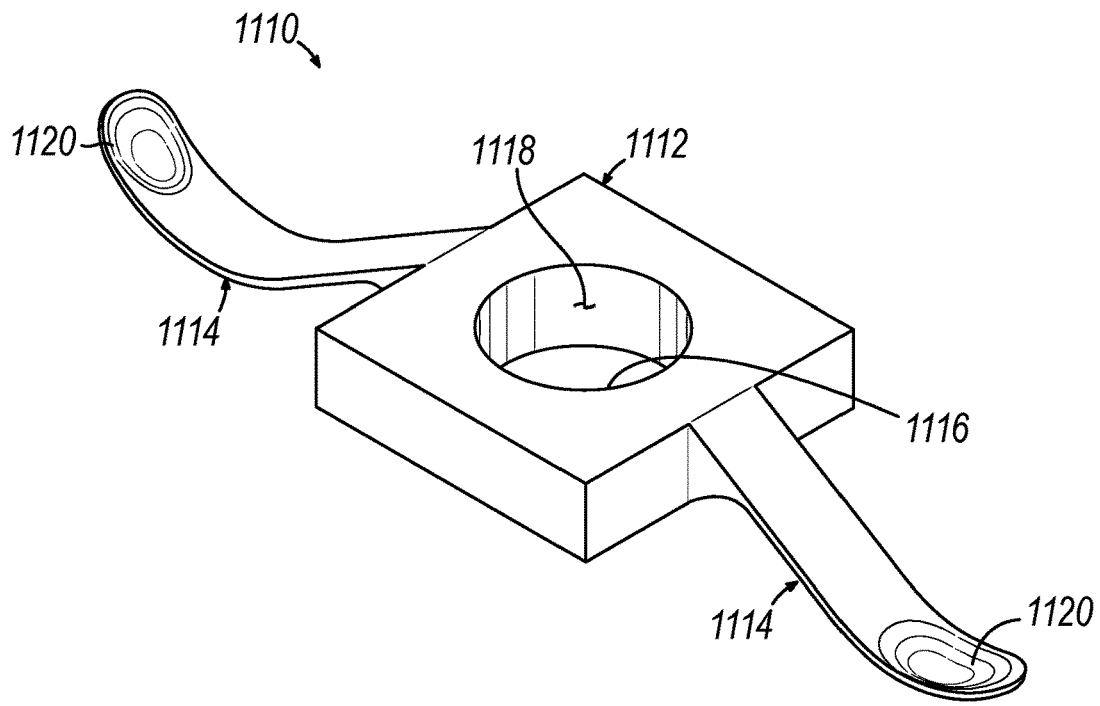
FIG. 14 depicts a perspective view of another exemplary depth limiter that includes two legs.

FIG. 14 shows a fourth exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 13A-13B.

E. Fifth Exemplary Depth Limiter

Figure 15:
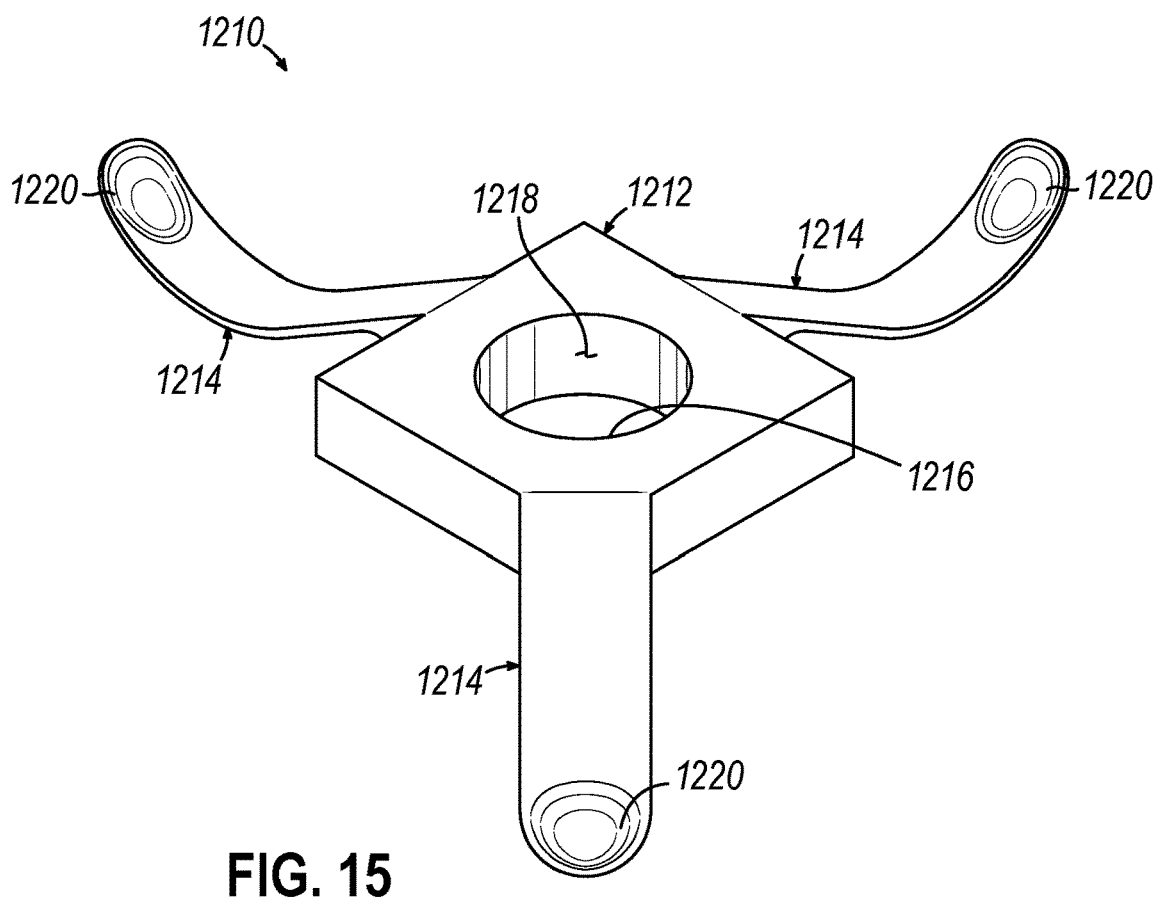
FIG. 15 depicts a perspective view of another exemplary depth limiter that includes three legs.

FIG. 15 shows a fifth exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 13A-13B.

F. Sixth Exemplary Depth Limiter

Figure 16:
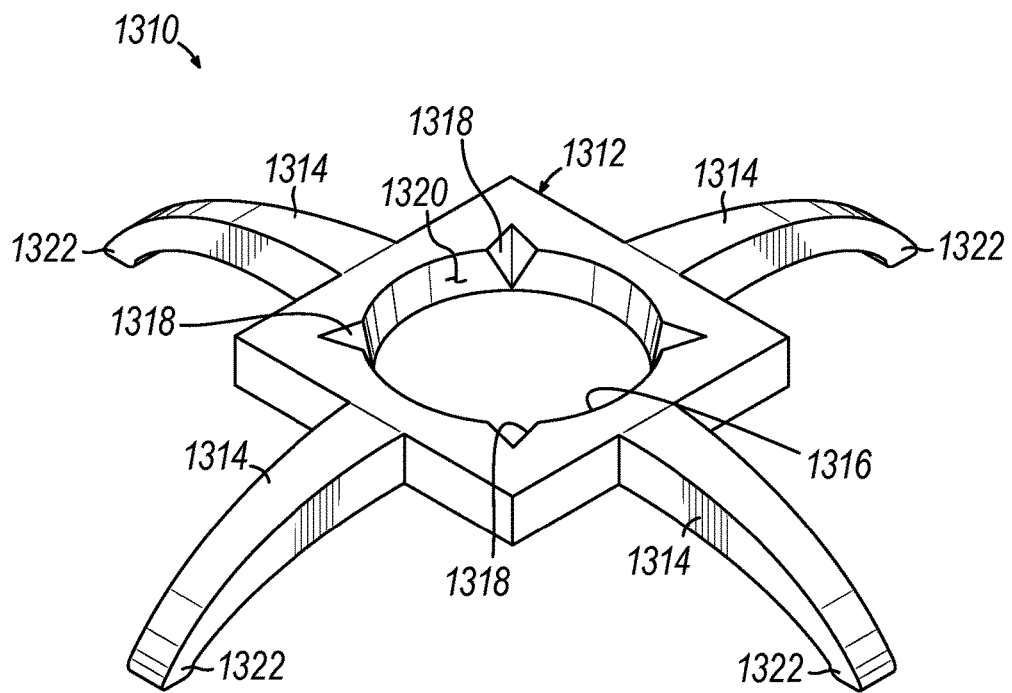
FIG. 16 depicts a perspective view of another exemplary depth limiter that includes a hub with notches.

FIGS. 16-18B show a sixth exemplary depth limiter (1310). Particularly, FIG. 16 shows a perspective view of depth limiter (1310). As shown, depth limiter (1310) includes a hub (1312) and a plurality of legs (1314). extending from hub (1312). Depth limiter (1310) may be used in combination with any one or more of depth limiters (200, 300) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). While FIGS. 17A-18B describe depth limiter (1310) with reference to cannula tube (124) of trocar (110), other cannula tubes (e.g., cannula tube (22)) may also be used. Gripping surface (1320) may be smooth or non-smooth. As shown in FIG. 16, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1322) to distribute the downward force. As shown, legs (1314) are separated by approximately 90 degrees. Legs (1314) may be non-uniformly separated. Additionally, more or fewer legs (1314) are also envisioned (similar to those shown in FIGS. 14-15 associated with depth limiters (1110, 1210). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120).

Figure 17A:
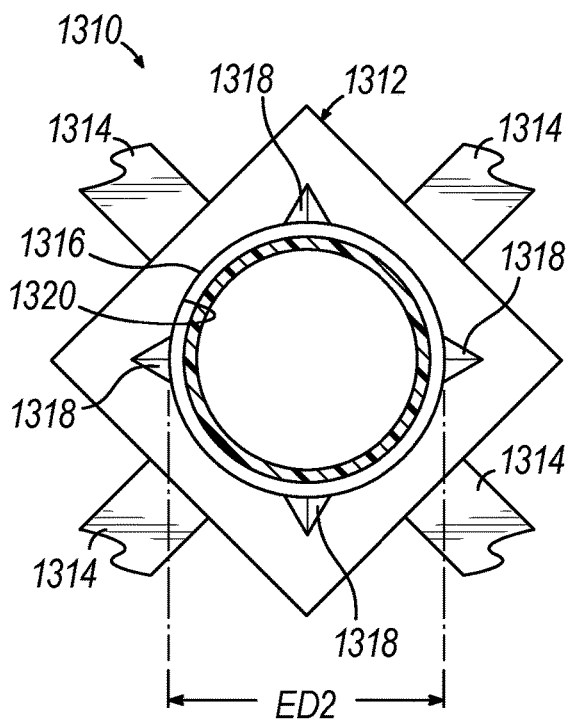
FIG. 17A depicts a top plan view of the depth limiter of FIG. 16 coupled with the cannula tube of the cannula assembly of FIG. 5, where the hub of the depth limiter is in a movable configuration.
Figure 18A:
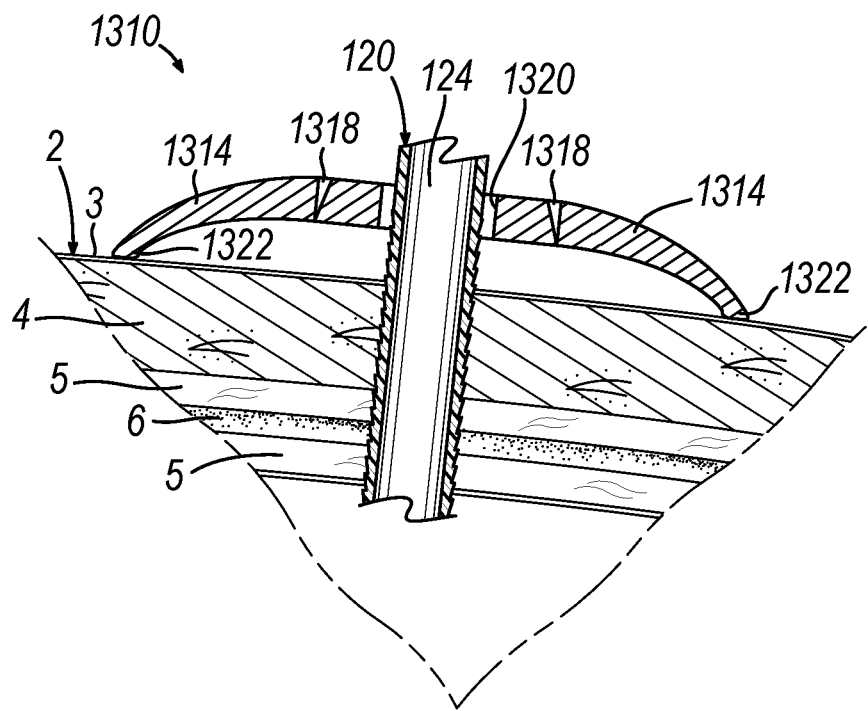
FIG. 18A depicts a partial side sectional view of the depth limiter of FIG. 16 coupled with the cannula tube of the cannula assembly of FIG. 5, where the legs of the depth limiter are in a deployed configuration.

FIGS. 17A and 18A show depth limiter (1310) in the movable configuration. Particularly, FIG. 17A shows a top plan view of depth limiter (1310) of FIG. 16 coupled with cannula tube (124) of cannula assembly (112) of FIG. 5, where hub (1312) of depth limiter (1310) is in a movable configuration. FIG. 18A shows a partial side sectional view of depth limiter (1310) of FIG. 16 coupled with cannula tube (124) of cannula assembly (112) of FIG. 5, where legs (1314) of depth limiter (1310) are in the movable configuration. In the movable configuration of FIGS. 17A and 18A, gripping surface (1320) forms a second effective diameter (ED2) that allows for axial movement of depth limiter (1310) relative to an outer diameter of cannula tube (124) of cannula (120). In the movable configuration, also considered the resting configuration, legs (1314) are curved downwardly. Once pushed against abdominal wall (2), legs (1314) bend flatter and provide a reaction force against abdominal wall (2) and cannula (120).

Figure 17B:
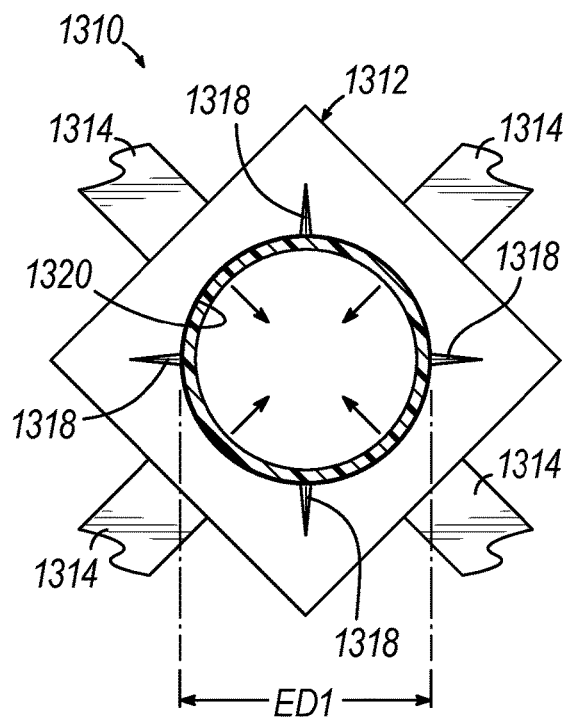
FIG. 17B depicts a partial side sectional view of the depth limiter of FIG. 16 coupled with the cannula tube of the cannula assembly of FIG. 5 following detachment and removal of the obturator, where the legs of the depth limiter are in a fixed configuration.
Figure 18B:
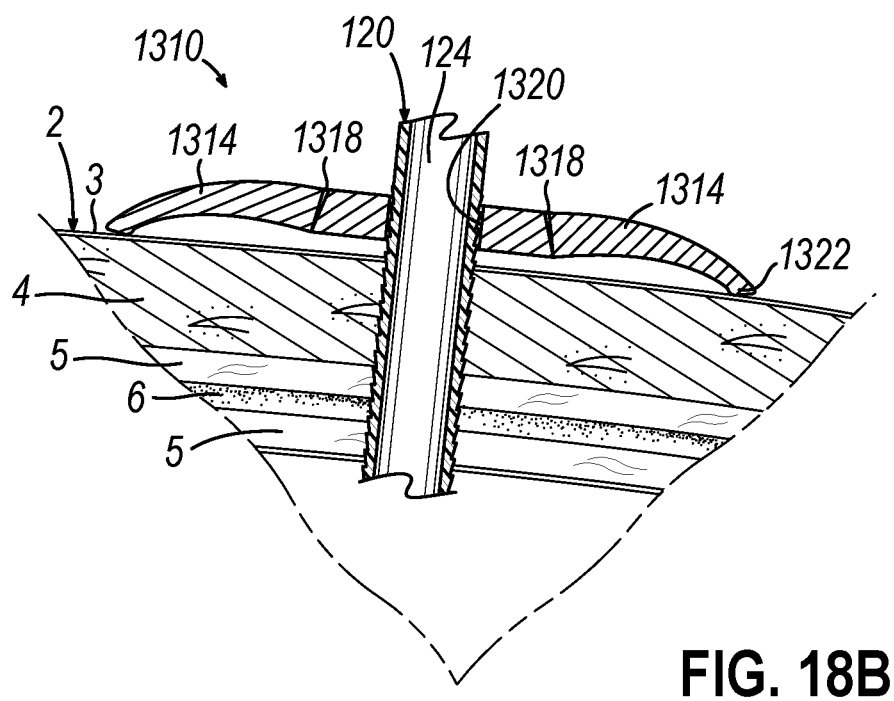
FIG. 18B depicts a partial side sectional view of the depth limiter of FIG. 16 coupled with the cannula tube of the cannula assembly of FIG. 5 following detachment and removal of the obturator, where the legs of the depth limiter are in a deployed configuration.

FIGS. 17B and 18B show depth limiter (1310) in the fixed configuration. Particularly, FIG. 17B shows a partial side sectional view of depth limiter (1310) of FIG. 16 coupled with cannula tube (124) of cannula assembly (112) of FIG. 5 following detachment and removal of obturator (116), where legs (1314) of depth limiter (1310) are in the fixed configuration. FIG. 18B shows a partial side sectional view of depth limiter (1310) of FIG. 16 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

G. Seventh Exemplary Depth Limiter

Figure 19:
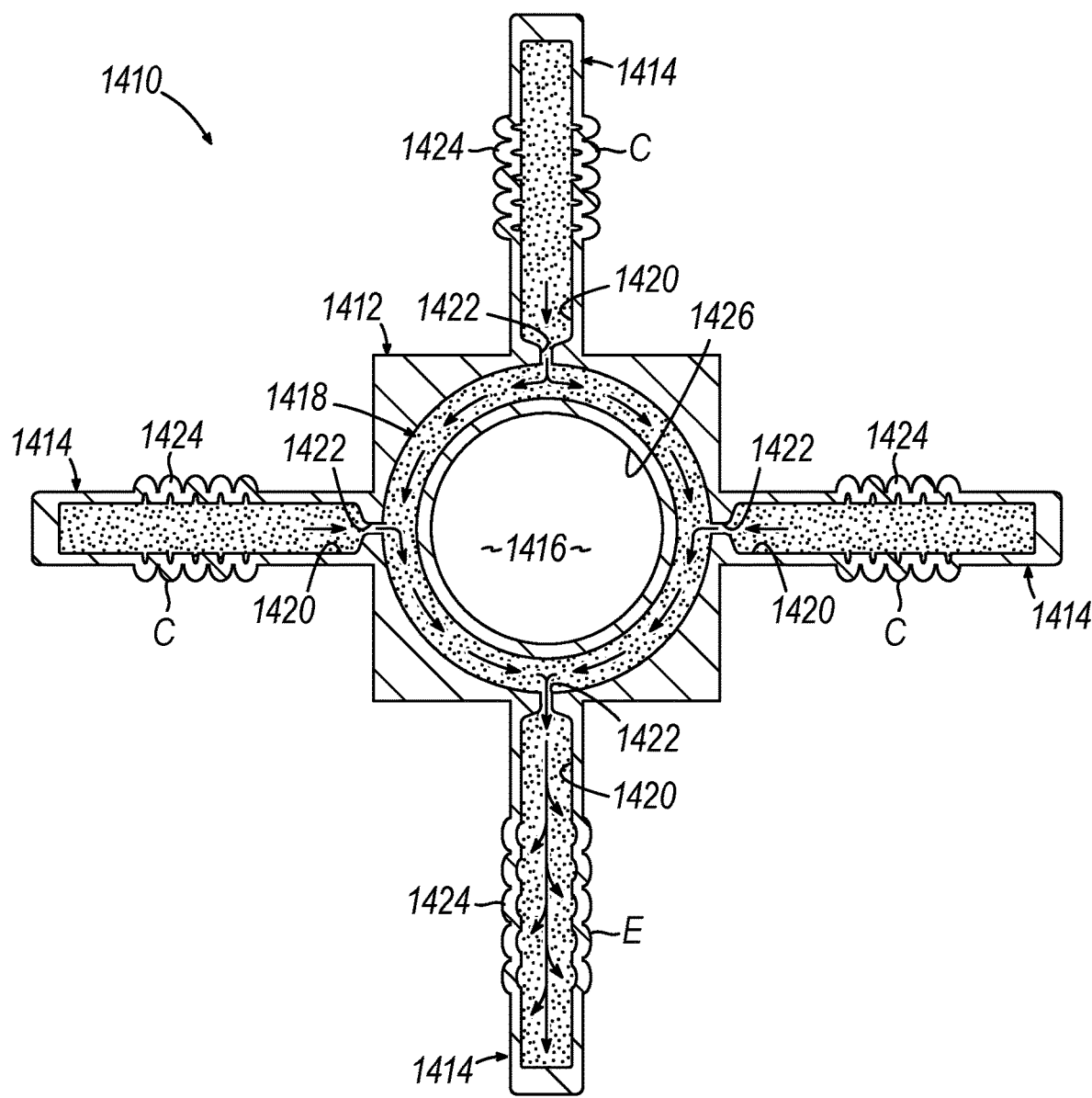
FIG. 19 depicts a top sectional view of another exemplary depth limiter that includes a fluid chamber and four legs.

FIG. 19 shows a top sectional view of a seventh exemplary depth limiter (1410). Depth limiter (1410) includes a hub (1412) and a plurality of legs (1414) extending from hub (1412). Depth limiter (1410) may be used in combination with any one or more of depth limiters (200, 300) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to depth limiters (1110, 1210) shown in FIGS. 14-15.

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these restricted areas (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 19, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A depth limiter configured to couple with a cannula tube of a trocar, the depth limiter comprising: (a) a body extending about a central axis and configured to encircle the cannula tube, wherein the body includes: (i) a first body portion, (ii) a second body portion opposed from the first body portion, wherein the first and second body portions are pivotably coupled together by a hinge such that the first and second body portions are pivotable relative to each other about the hinge between an open configuration and a clamped configuration, (iii) a first inner surface presented by the first body portion, and (iv) a second inner surface presented by the second body portion, wherein in the clamped configuration the first and second inner surfaces collectively form a first effective cross dimension transverse to the central axis and sized to restrict axial movement of the depth limiter relative to the cannula tube of the trocar, wherein in the open configuration the first and second inner surfaces collectively form a second effective cross dimension transverse to the central axis and sized to permit axial movement of the depth limiter relative to the cannula tube of the trocar; (b) a first locking member extending from the first body portion toward the second body portion; and (c) a second locking member positioned within the second body portion, wherein at least one of the first or second locking members is resiliently biased to engage the other of the first or second locking members, wherein in the clamped configuration the first and second locking members are configured to engage each other to selectively lock the first and second body portions in the clamped configuration.

Example 2

The depth limiter of Example 1, wherein the first locking member includes a pawl, wherein the pawl is biased radially outwardly relative to the central axis.

Example 3

The depth limiter of Example 2, wherein the second locking member includes a rack, wherein in the clamped configuration the rack is configured to engage the pawl to selectively lock the first and second body portions in the clamped configuration.

Example 4

The depth limiter of Example 3, wherein the pawl includes a pawl tooth directed radially outwardly relative to the central axis and having a first locking surface and a first camming surface, wherein the rack includes at least one rack tooth directed radially inwardly relative to the central axis and having a second locking surface and a second camming surface.

Example 5

The depth limiter of Example 4, wherein the first and second camming surfaces are configured to engage with each other to at least partially redirect movement of the pawl tooth relative to the rack and thereby allow approximation of the first and second body portions toward the clamped configuration, wherein the first and second locking surfaces are configured to engage with each other to arrest movement of the pawl tooth relative to the rack and thereby inhibit separation of the first and second body portions toward the open configuration.

Example 6

The depth limiter of any of the preceding Examples, further comprising a release button configured to selectively engage at least one of the first or second locking members to disengage the first and second locking members from each other and thereby allow movement of the first and second body portions toward the open configuration.

Example 7

The depth limiter of Example 6, wherein at least one of the first or second locking members includes a release tab, wherein the release button includes a protrusion directly radially inwardly relative to the central axis and configured to selectively engage the release tab to disengage the first and second locking members from each other and thereby allow movement of the first and second body portions toward the open configuration.

Example 8

The depth limiter of any of the preceding Examples, wherein the first locking member extends into an interior cavity of the second body portion.

Example 9

The depth limiter of any of the preceding Examples, further comprising first and second outer surfaces positioned on the first and second body portions, respectively, and including diametrically opposed first and second finger grips, respectively.

Example 10

The depth limiter of Example 9, wherein the first body portion extends between a first hinged end and a first occluding end, wherein the second body portion extends between a second hinged end and a second occluding end, wherein the first finger grip is positioned centrally between the first hinged end and the first occluding end, wherein the second finger grip is positioned centrally between the second hinged end and the second occluding end.

Example 11

The depth limiter of any of the preceding Examples, wherein at least one of the first or second inner surfaces includes at least one tube gripping feature configured to grip the cannula tube of the trocar.

Example 12

The depth limiter of any of the preceding Examples, wherein the first and second body portions are biased toward the open configuration.

Example 13

The depth limiter of any of the preceding Examples, wherein the hinge includes a living hinge.

Example 14

The depth limiter of Example 13, wherein the first and second body portions and the living hinge are integrally formed together as a unitary piece.

Example 15

The depth limiter of Example 14, wherein the unitary piece comprises a plastic material.

Example 16

A surgical access device assembly comprising: (a) a cannula including a working channel configured to guide a surgical instrument along a central axis of the cannula; and (b) a depth limiter movably coupled with the cannula and including: (i) a body extending about a central axis of the depth limiter and encircling the cannula, wherein the body includes: (A) first and second body portions opposed from each other and pivotably coupled together by a hinge such that the first and second body portions are pivotable relative to each other about the hinge between an open configuration and a clamped configuration, and (B) first and second inner surfaces presented by the first and second body portions, respectively, wherein in the clamped configuration the first and second inner surfaces collectively form a first effective cross dimension transverse to the central axis sized to restrict axial movement of the depth limiter relative to the cannula, wherein in the open configuration the first and second inner surfaces collectively form a second effective cross dimension transverse to the central axis sized to permit axial movement of the depth limiter relative to the cannula, (ii) a first locking member extending from the first body portion toward the second body portion, and (iii) a second locking member positioned within the second body portion, wherein at least one of the first or second locking members is resiliently biased to engage the other of the first or second locking members, wherein in the clamped configuration the first and second locking members are configured to engage each other to selectively lock the first and second body portions in the clamped configuration.

Example 17

The surgical access device assembly of Example 16, wherein the first locking member includes a first tooth directed radially outwardly relative to the central axis of the depth limiter and having a first locking surface and a first camming surface, wherein the second locking member includes a second tooth directed radially inwardly relative to the central axis of the depth limiter and having a second locking surface and a second camming surface.

Example 18

The surgical access device assembly of Example 17, wherein the first and second camming surfaces are configured to engage with each other to at least partially redirect movement of the first locking member relative to the second locking member and thereby allow movement of the first and second body portions toward the clamped configuration, wherein the first and second locking surfaces are configured to engage with each other to arrest movement of the first locking member relative to the second locking member and thereby inhibit movement of the first and second body portions toward the open configuration.

Example 19

A method of using a depth limiter with a trocar, wherein the depth limiter includes first and second body portions pivotably coupled to each other by a hinge, first and second inner surfaces positioned on the first and second body portions, respectively, a first locking member extending from the first body portion toward the second body portion, and a second locking member positioned within the second body portion, wherein at least one of the first or second locking members is resiliently biased to engage the other of the first and second locking members, the method comprising: (a) positioning the first and second body portions at least partially about a cannula tube of a trocar such that the first and second body portions are in an open configuration; and (b) pivoting the first and second body portions relative to each other about the hinge from the open configuration toward a clamped configuration about the cannula tube, wherein in the clamped configuration the first and second inner surfaces collectively form a first effective cross dimension that restricts axial movement of the depth limiter relative to the cannula tube of the trocar, wherein in the open configuration the first and second inner surfaces collectively form a second effective cross dimension that allows for axial movement of the depth limiter relative to the cannula tube of the trocar, wherein in the clamped configuration the first and second locking members engage each other to selectively lock the first and second body portions in the clamped configuration.

Example 20

The method of Example 19, wherein the depth limiter has a release button, the method further comprising selectively engaging at least one of the first or second locking members with the release button to disengage the first and second locking members from each other and thereby allow movement of the first and second body portions toward the open configuration:

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, issued as U.S. Pat. No. Aug. 1, 2023; U.S. patent application Ser. No. 17/213,431, entitled "Two Piece Separable Obturator," filed on Mar. 26, 2021, published as U.S. Pub. No. 2021/0338275 on Nov. 4, 2021; U.S. patent application Ser. No. 17/213,434, entitled "Latchless Obturator with Interference Fit Feature," filed on Mar. 26, 2021, published as U.S. Pub. No. 2021/0338269 Nov. 4, 2021; U.S. patent application Ser. No. 17/213,437, entitled "Balancing Feature for Reusable Trocar," filed on Mar. 26, 2021, issued as U.S. Pat. No. 11,559,329 Jan. 24, 2023; U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A depth limiter configured to couple with a cannula tube of a trocar, the depth limiter comprising:
   (a) a body extending about a central axis and configured to encircle the cannula tube, wherein the body includes:
      (i) a first body portion,
      (ii) a second body portion opposed from the first body portion, wherein the first and second body portions are pivotably coupled together by a hinge such that the first and second body portions are pivotable relative to each other about the hinge between an open configuration and a clamped configuration,
      (iii) a first inner surface presented by the first body portion, and
      (iv) a second inner surface presented by the second body portion, wherein in the clamped configuration the first and second inner surfaces collectively form a first effective cross dimension transverse to the central axis and sized to restrict axial movement of the depth limiter relative to the cannula tube of the trocar, wherein in the open configuration the first and second inner surfaces collectively form a second effective cross dimension transverse to the central axis and sized to permit axial movement of the depth limiter relative to the cannula tube of the trocar;
   (b) a first locking member extending from the first body portion toward the second body portion; and
   (c) a second locking member positioned within the second body portion,
   wherein at least one of the first or second locking members is resiliently biased to engage the other of the first or second locking members, wherein in the clamped configuration the first and second locking members are configured to engage each other to selectively lock the first and second body portions in the clamped configuration,
   wherein the first locking member includes a pawl, wherein the pawl is biased radially outwardly relative to the central axis.

2. The depth limiter of claim 1, wherein the second locking member includes a rack, wherein in the clamped configuration the rack is configured to engage the pawl to selectively lock the first and second body portions in the clamped configuration.

3. The depth limiter of claim 2, wherein the pawl includes a pawl tooth directed radially outwardly relative to the central axis and having a first locking surface and a first camming surface, wherein the rack includes at least one rack tooth directed radially inwardly relative to the central axis and having a second locking surface and a second camming surface.

4. The depth limiter of claim 3, wherein the first and second camming surfaces are configured to engage with each other to at least partially redirect movement of the pawl tooth relative to the rack and thereby allow approximation of the first and second body portions toward the clamped configuration, wherein the first and second locking surfaces are configured to engage with each other to arrest movement of the pawl tooth relative to the rack and thereby inhibit separation of the first and second body portions toward the open configuration.

5. The depth limiter of claim 1, further comprising a release button configured to selectively engage at least one of the first or second locking members to disengage the first and second locking members from each other and thereby allow movement of the first and second body portions toward the open configuration.

6. The depth limiter of claim 5, wherein at least one of the first or second locking members includes a release tab, wherein the release button includes a protrusion directly radially inwardly relative to the central axis and configured to selectively engage the release tab to disengage the first and second locking members from each other and thereby allow movement of the first and second body portions toward the open configuration.

7. The depth limiter of claim 1, wherein the first locking member extends into an interior cavity of the second body portion.

8. The depth limiter of claim 1, further comprising first and second outer surfaces positioned on the first and second body portions, respectively, and including diametrically opposed first and second finger grips, respectively.

9. The depth limiter of claim 8, wherein the first body portion extends between a first hinged end and a first occluding end, wherein the second body portion extends between a second hinged end and a second occluding end, wherein the first finger grip is positioned centrally between the first hinged end and the first occluding end, wherein the second finger grip is positioned centrally between the second hinged end and the second occluding end.

10. The depth limiter of claim 1, wherein at least one of the first or second inner surfaces includes at least one tube gripping feature configured to grip the cannula tube of the trocar.

11. The depth limiter of claim 1, wherein the first and second body portions are biased toward the open configuration.

12. The depth limiter of claim 1, wherein the hinge includes a living hinge.

13. The depth limiter of claim 12, wherein the first and second body portions and the living hinge are integrally formed together as a unitary piece.

14. The depth limiter of claim 13, wherein the unitary piece comprises a plastic material.

15. The depth limiter of claim 1, wherein the pawl extends circumferentially from the first body portion along a curved path.

16. The depth limiter of claim 1, further comprising first and second outer surfaces positioned on the first and second body portions, respectively, wherein the first and second outer surfaces are each generally semi-circular, wherein the pawl is disposed radially inwardly of the first and second outer surfaces relative to the central axis.

17. A surgical access device assembly comprising:
(a) a cannula including a working channel configured to guide a surgical instrument along a central axis of the cannula; and
(b) a depth limiter movably coupled with the cannula and including:
  (i) a body extending about a central axis of the depth limiter and encircling the cannula, wherein the body includes:
    (A) first and second body portions opposed from each other and pivotably coupled together by a hinge such that the first and second body portions are pivotable relative to each other about the hinge between an open configuration and a clamped configuration, and
    (B) first and second inner surfaces presented by the first and second body portions, respectively, wherein in the clamped configuration the first and second inner surfaces collectively form a first effective cross dimension transverse to the central axis sized to restrict axial movement of the depth limiter relative to the cannula, wherein in the open configuration the first and second inner surfaces collectively form a second effective cross dimension transverse to the central axis sized to permit axial movement of the depth limiter relative to the cannula,
  (ii) a first locking member extending from the first body portion toward the second body portion, and
  (iii) a second locking member positioned within the second body portion,
  wherein at least one of the first or second locking members is resiliently biased to engage the other of the first or second locking members, wherein in the clamped configuration the first and second locking members are configured to engage each other to selectively lock the first and second body portions in the clamped configuration,
  wherein the first and second body portions are biased toward the open configuration.

18. The surgical access device assembly of claim 17, wherein the first locking member includes a first tooth directed radially outwardly relative to the central axis of the depth limiter and having a first locking surface and a first camming surface, wherein the second locking member includes a second tooth directed radially inwardly relative to the central axis of the depth limiter and having a second locking surface and a second camming surface.

19. The surgical access device assembly of claim 18, wherein the first and second camming surfaces are configured to engage with each other to at least partially redirect movement of the first locking member relative to the second locking member and thereby allow movement of the first and second body portions toward the clamped configuration, wherein the first and second locking surfaces are configured to engage with each other to arrest movement of the first locking member relative to the second locking member and thereby inhibit movement of the first and second body portions toward the open configuration.

20. A method of using a depth limiter with a trocar, wherein the depth limiter includes first and second body portions pivotably coupled to each other by a hinge, first and second inner surfaces positioned on the first and second body portions, respectively, a first locking member extending from the first body portion toward the second body portion, and a second locking member positioned within the second body portion, wherein at least one of the first or second locking members is resiliently biased to engage the other of the first and second locking members, wherein the depth limiter has a release button, the method comprising:
(a) positioning the first and second body portions at least partially about a cannula tube of a trocar such that the first and second body portions are in an open configuration;
(b) pivoting the first and second body portions relative to each other about the hinge from the open configuration toward a clamped configuration about the cannula tube; and
(c) selectively engaging at least one of the first or second locking members with the release button to disengage the first and second locking members from each other and thereby allow movement of the first and second body portions toward the open configuration, wherein selectively engaging the at least one of the first or second locking members with the release button includes depressing at least a portion of the release button radially inwardly toward the cannula tube,
wherein in the clamped configuration the first and second inner surfaces collectively form a first effective cross dimension that restricts axial movement of the depth limiter relative to the cannula tube of the trocar,
wherein in the open configuration the first and second inner surfaces collectively form a second effective cross dimension that allows for axial movement of the depth limiter relative to the cannula tube of the trocar,
wherein in the clamped configuration the first and second locking members engage each other to selectively lock the first and second body portions in the clamped configuration.

* * * * *

UNITED STATES PATENT AND TRADEMARK OFFICE
CERTIFICATE OF CORRECTION

| | | |
|---|---|---|
| PATENT NO. | : 11,980,392 B2 | Page 1 of 1 |
| APPLICATION NO. | : 17/213401 | |
| DATED | : May 14, 2024 | |
| INVENTOR(S) | : Vijayachandran et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Eighth Day of October, 2024

Katherine Kelly Vidal
*Director of the United States Patent and Trademark Office*